(12) United States Patent
Ahmed

(10) Patent No.: US 11,572,329 B1
(45) Date of Patent: Feb. 7, 2023

(54) SYSTEM AND METHOD FOR METHANOL PRODUCTION USING ENERGY MIX SYSTEMS

(71) Applicant: King Fahd University of Petroleum and Minerals, Dhahran (SA)

(72) Inventor: Usama Ahmed, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 17/730,400

(22) Filed: Apr. 27, 2022

Related U.S. Application Data

(60) Provisional application No. 63/281,921, filed on Nov. 22, 2021.

(51) Int. Cl.
*C07C 29/151* (2006.01)
*C01B 3/48* (2006.01)
(Continued)

(52) U.S. Cl.
CPC ....... *C07C 29/1518* (2013.01); *B01J 19/0013* (2013.01); *B01J 19/245* (2013.01);
(Continued)

(58) Field of Classification Search
CPC .... B01J 2208/00309; C01B 2203/1241; C01B 2203/0244; C01B 2203/061;
(Continued)

(56) References Cited

U.S. PATENT DOCUMENTS

| | | | | |
|---|---|---|---|---|
| 4,242,458 A | * | 12/1980 | Child | C07C 29/1518 |
| | | | | 435/930 |
| 4,315,900 A | * | 2/1982 | Nozawa | C07C 29/1518 |
| | | | | 518/704 |

(Continued)

FOREIGN PATENT DOCUMENTS

| | | | | |
|---|---|---|---|---|
| CN | 101191084 B | | 12/2010 | |
| JP | 8-99921 | | 4/1996 | |
| WO | WO-2020150247 A1 | * | 7/2020 | B01D 53/265 |

OTHER PUBLICATIONS

Lin, et al. ; A new polygeneration system for methanol and power based on coke oven gas and coal gas ; Proceedings of ECOS 2012—The 25th International Conference on Efficiency, Cost, Optimization, Simulation and Environmental Impact of Energy Systems ; Jun. 26-29, 2012.

(Continued)

*Primary Examiner* — Imran Akram
(74) *Attorney, Agent, or Firm* — Oblon, McClelland, Maier & Neustadt, L.L.P.

(57) ABSTRACT

A system and a method for methanol production is described. The method includes gasifying coal to produce a coal gas comprising hydrogen and carbon monoxide; transferring heat from the coal gas to a natural gas reforming mixture including water and methane; reforming the natural gas reforming mixture to form a reformed natural gas; mixing the coal gas, the reformed natural gas, and a recycled gas including hydrogen and carbon monoxide to form a synthesis gas; reacting the synthesis gas to form methanol and a waste gas; separating the methanol and the waste gas; removing hydrogen from the waste gas to produce a dehydrogenated waste gas; and subjecting the dehydrogenated waste gas to a water-gas shift reaction to produce the recycled gas.

17 Claims, 9 Drawing Sheets

(51) Int. Cl.
   *B01J 19/24* (2006.01)
   *B01J 19/00* (2006.01)
   *C10J 3/82* (2006.01)
   *C07C 29/152* (2006.01)
(52) U.S. Cl.
   CPC ............ *B01J 19/2465* (2013.01); *C01B 3/48* (2013.01); *C07C 29/152* (2013.01); *C10J 3/82* (2013.01); *B01J 2219/00117* (2013.01); *C01B 2203/0233* (2013.01); *C01B 2203/0283* (2013.01); *C01B 2203/0475* (2013.01); *C01B 2203/061* (2013.01); *C01B 2203/1241* (2013.01); *C01B 2203/148* (2013.01); *C10J 2300/1612* (2013.01); *C10J 2300/1618* (2013.01); *C10J 2300/1665* (2013.01)
(58) Field of Classification Search
   CPC .......... C10J 2300/093; C10J 2300/1618; C10J 2300/1665
   See application file for complete search history.

(56) References Cited

U.S. PATENT DOCUMENTS

| | | | | |
|---|---|---|---|---|
| 4,526,903 | A * | 7/1985 | Cummings | ......... C07C 29/1518 48/214 R |
| 8,152,874 | B2 | 4/2012 | Briesch et al. | |
| 11,053,119 | B2 | 7/2021 | Ostuni et al. | |
| 2002/0159929 | A1 * | 10/2002 | Kaneko | .................... C10K 1/08 48/199 FM |
| 2005/0256212 | A1 * | 11/2005 | Norbeck | .................. C10J 3/723 518/702 |
| 2007/0289214 | A1 * | 12/2007 | Briesch | ................... C01B 3/323 422/600 |
| 2008/0279763 | A1 * | 11/2008 | Snyder | ..................... C01B 3/48 423/648.1 |
| 2009/0324458 | A1 * | 12/2009 | Robinson | ............... C10K 1/004 422/187 |
| 2011/0124927 | A1 * | 5/2011 | Stites | ..................... C07C 67/37 568/907 |
| 2012/0014851 | A1 * | 1/2012 | Kloosterman | ........... C10K 1/32 423/437.1 |
| 2012/0145965 | A1 * | 6/2012 | Simmons | .............. C07C 29/152 422/162 |
| 2012/0181483 | A1 * | 7/2012 | Simmons | ................... C10J 3/62 252/373 |
| 2013/0030063 | A1 * | 1/2013 | Randhava | .............. C10K 1/003 518/703 |
| 2014/0080928 | A1 * | 3/2014 | Kelfkens | ............. C07C 29/1518 518/704 |
| 2017/0037328 | A1 | 2/2017 | Wormser et al. | |
| 2017/0044013 | A1 * | 2/2017 | Kelly | ........................ B01J 7/02 |
| 2018/0135004 | A1 * | 5/2018 | Bradin | .................... C12P 7/649 |
| 2019/0119182 | A1 * | 4/2019 | McCormick | ............... C07C 7/12 |
| 2022/0119328 | A1 * | 4/2022 | Schroer | ............... H01M 8/0612 |

OTHER PUBLICATIONS

Ahmed, et al.; Techno-Economic Assessment of Conceptual Design for Methanol Production Using Coal and Natural Gas Based Parallel Process Configuration; Computer Aided Chemical Engineering, vol. 48; pp. 1441-1446; Oct. 19, 2020.

\* cited by examiner

SYSTEM AND METHOD FOR METHANOL PRODUCTION USING ENERGY MIX SYSTEMS

CROSS-REFERENCE TO RELATED APPLICATION

The present application claims priority to U.S. Provisional Application No. 63/281,921, filed Nov. 22, 2021, the teaching of which is hereby incorporated by reference in its entirety for all purposes.

STATEMENT OF PRIOR DISCLOSURE BY THE INVENTORS

Aspects of the present disclosure are described in the article "Techno-Economic Analysis of Dual Methanol and Hydrogen Production Using Energy Mix Systems with $CO_2$ Capture" published in Energy Conversion and Management 2021, Vol 228, 113663, available on Nov. 20, 2020, which is incorporated herein by reference in its entirety.

BACKGROUND

Technical Field

The present disclosure is directed to energy conversion and management, particularly to an energy conversion system and method for dual methanol and hydrogen production using mixed energy input systems.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

In the last decades, fossil fuels have been the primary source of energy and power generation. An increased emission of greenhouse gas has lead to unsafe levels of pollutants and global warming. The damage caused by fossil fuels to the environment, especially by coal-based systems, may be minimized using alternative energy conversion technologies. Conventionally, natural gas and coal-based processes have been used for methanol production and electricity generation. Generally, methanol synthesis reactions are exothermic, generating a large amount of heat. The evolved heat is usually used to generate steam and electricity using a Rankine cycle. A carbon conversion efficiency measurement estimates the percentage of synthesis gas conversion into methanol. In conventional methods, unconverted synthesis gas is mainly recycled in a methanol synthesis reactor. In certain methods, the unconverted synthesis gas containing CO and $H_2$ is sent to a combustion unit for heat and power generation. However, this process is energy and capital-intensive, making it an inefficient approach to energy utilization. Therefore, there exists a need to develop more energy efficient, resource efficient, and lower emission methods for a dual production of methanol and hydrogen.

Accordingly, it is one object of the present disclosure to provide a method and system for methanol and hydrogen co-production which overcomes the limitations of the art discussed above.

SUMMARY

The present disclosure relates to a method of synthesizing methanol. The method of preparing methanol includes gasifying coal to produce a coal gas including hydrogen and carbon monoxide and transferring heat from the coal gas to a natural gas reforming mixture including water and methane, thereby cooling the coal gas and heating the natural gas reforming mixture. The method further includes reforming the natural gas reforming mixture to form a reformed natural gas including hydrogen and carbon monoxide and mixing the coal gas, the reformed natural gas, and a recycled gas including hydrogen and carbon monoxide to form a synthesis gas. Furthermore, the method includes reacting the synthesis gas to form the methanol and a waste gas including water, carbon monoxide, and carbon dioxide. The method further includes separating the methanol and the waste gas, then removing hydrogen from the waste gas to produce a dehydrogenated waste gas, and further subjecting the dehydrogenated waste gas to a water-gas shift reaction to produce the recycled gas.

In some embodiments, the method further includes removing sulfur-containing species from the coal gas before mixing.

In some embodiments, the method further includes removing carbon dioxide from the synthesis gas before reacting the synthesis gas to form methanol and the waste gas.

In some embodiments, the method includes gasifying coal at 1200 to 1550 degrees centigrade (° C.) and 45 to 67 bar to produce the coal gas.

In some embodiments, the method includes reforming the natural gas reforming mixture, which is performed at 900 to 1200° C. and 32 to 68 bar to form the reformed natural gas.

In some embodiments, the method includes reacting the synthesis gas at 125 to 275° C. and 45 to 65 bar to form methanol and the waste gas.

In some embodiments, the synthesis gas has a hydrogen to carbon ratio of 45:55 to 55:45 and a higher heating value (HHV) of 16.5 to 20.5 megajoules per kilogram (MJ/kg).

In some embodiments, the method has a carbon conversion efficiency of 32.5 to 47.5%.

In some embodiments, the method has a production energy of 34 to 40 gigajoules per metric ton (GJ/Mt) total fuel, the total fuel being the sum of the ethanol and hydrogen produced.

In some embodiments, the method has a process efficiency of about 66 to 74, the process efficiency calculated by:

$$\text{Process Efficiency}(\eta net) = \frac{\text{Methanol theral energy } [MWth] \text{ H2 thermal energy}[MWth]}{\text{Feed stock thermal energy } [MWth] + \text{Energy consumed}[MWth]} \times 100$$

The present disclosure also relates to a methanol production system. The system includes a coal gasification unit configured to receive a gasifier input stream, including coal and water, and further convert the gasifier input stream to the coal gas, including hydrogen and carbon monoxide, to provide a coal gas stream. The system further includes a natural gas reforming unit configured to receive a natural gas input stream and a waste heat output, and further reform the natural gas to produce the reformed natural gas, including hydrogen and carbon monoxide, and provide a reformed gas stream. The system further includes a heat exchanger configured to transfer heat from the coal gas stream to the natural gas input stream, thereby cooling the coal gas and heating the natural gas input stream. Furthermore, the system includes a syngas mixer configured to receive the coal gas stream, the reformed gas stream, and a recycled gas stream, and provide a syngas stream including a synthesis gas. The synthesis gas includes hydrogen and carbon monoxide. The system further includes a methanol reaction unit configured to receive the syngas stream, and further react the syngas stream to form methanol and the waste gas, including water, carbon monoxide, and carbon dioxide. The methanol reaction unit is further configured to provide a methanol output stream, including the methanol and a waste gas stream. The system further includes a recycling unit configured to receive the waste gas stream, remove hydrogen from the waste gas to produce the dehydrogenated waste gas and hydrogen, and further subject the dehydrogenated waste gas to the water-gas shift reaction to produce the recycled gas, and provide the recycled gas stream.

In some embodiments, the system further includes a sulfur remover disposed between the coal gasification unit and the syngas mixer, configured to remove sulfur-containing species from the coal gas before mixing the coal gas, the reformed natural gas, and a recycled gas to form the synthesis gas.

In some embodiments, the system further includes a syngas/carbon dioxide remover disposed between the syngas mixer and the methanol reaction unit. The syngas remover is configured to remove carbon dioxide from the synthesis gas before reacting the synthesis gas to form methanol and the waste gas.

In some embodiments, the gasifier input stream is converted to coal at 1200 to 1550° C. and 45 to 67 bars.

In some embodiments, the natural gas is reformed to the reformed gas at 900 to 1200° C. and 32 to 68 bar.

In some embodiments, syngas is reacted at 125 to 275° C. and 45 to 65 bars.

In some embodiments, the syngas has the hydrogen to carbon ratio of 45:55 to 55:45 and the HHV of 16.5 to 20.5 mJ/kg.

In some embodiments, the system has a carbon conversion efficiency of 32.5 to 47.5%.

In some embodiments, the system has production energy of 34 to 40 GJ/Mt total fuel, the total fuel being the sum of the methanol and hydrogen produced.

In some embodiments, the system has a process efficiency of 66 to 74%, the process efficiency calculated by:

$$\text{Process Efficiency}(\eta net) = \frac{\text{Methanol thermal energy } [MWth] + \text{H2 thermal energy}[MWth]}{\text{Feed stock thermal energy } [MWth] + \text{Energy consumed}[MWth]} \times 100$$

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
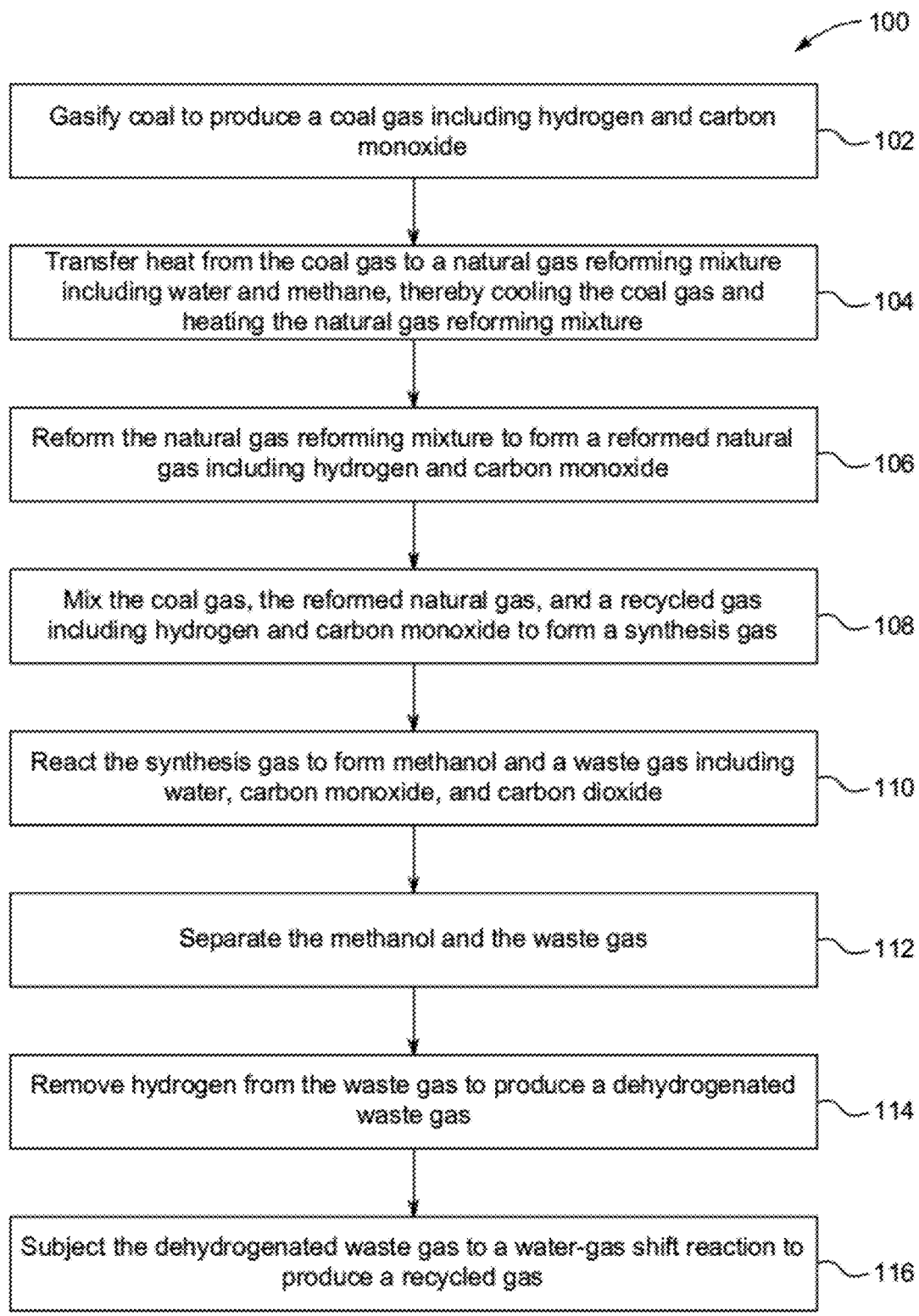
FIG. 1 is a schematic flow diagram of a method of preparing methanol, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

As used herein, the term, "water-gas shift reaction" refers to a reversible reaction of carbon monoxide and water vapor to form carbon dioxide and hydrogen, according to the formula below:

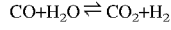

$CO+H_2O \rightleftharpoons CO_2+H_2$

As used herein, the term, "gasification" refers to a process that converts biomass or fossil fuel-based carbonaceous materials into gases, including nitrogen, carbon monoxide, hydrogen, and carbon dioxide as the largest fractions.

As used herein, the term, "syngas" or "synthesis gas" refers to a fuel gas mixture comprising predominantly (i.e. greater than 51% of a number of moles of the syngas)

hydrogen and carbon monoxide, with the rest of the mixture being comprised of other gases such as carbon dioxide, water vapor, methane, hydrogen sulfide, methanethiol, and carbon disulfide. Typically, syngas comprises greater than 70% hydrogen and carbon monoxide by mole.

As used herein, the term, "techno-economic" refers to a method of analyzing the economic performance of an industrial process, product, or service.

As used herein, the term, "Claus plant" refers to a de-sulfurizing process which involves recovering elemental sulfur from gaseous hydrogen sulfide.

As used herein, the term, "case 1 system" and "case 1" may be used interchangeably throughout the draft.

As used herein, the term, "case 2 system" and "case 2" may be used interchangeably throughout the draft.

Embodiments of the present disclosure are directed towards a system and a method of dual methanol and hydrogen production. Where appropriate, specific comparison between the system of the present disclosure and a conventional methanol synthesis system will be made. Such specific comparison is intended to highlight specific differences and advantages of the system of the present disclosure. The conventional methanol synthesis system may be referred to as a "case 1 system" or "case 1", while the system of the present disclosure may be referred to as a "case 2 system" or "case 2" where appropriate.

Referring to FIG. 1, a schematic flow diagram of the method 100 of preparing methanol is illustrated according to some embodiments. The order in which the method 100 is described is not intended to be construed as a limitation, and any number of the described method steps may be combined in any order to implement the method 100. Additionally, individual steps may be removed or skipped from the method 100 without departing from the spirit and scope of the present disclosure.

At step 102, the method 100 includes gasifying coal to produce a coal gas, including hydrogen and carbon monoxide. In some embodiments, the coal gas may include a mixture of calorific gases including hydrogen, carbon monoxide, methane, ethylene, and other volatile hydrocarbons together with small quantities of non-calorific gases such as carbon dioxide and nitrogen.

In general, the gasifying can be performed using any suitable equipment or by any suitable technique known to one of ordinary skill in the art. The gasifying may be performed with an atmosphere of ambient air or an oxygen-rich atmosphere, for example ambient air with added oxygen or a mixture comprising oxygen and a suitable inert gas. The gasifying can involve coal and any suitable additional gasification reactants. Typically, gasifying of coal is performed with added water. Such added water may be useful in, for example providing additional hydrogen or allowing certain products or intermediates of the gasification to undergo the water-gas shift reaction described above. There is no specific limitation on the type or composition of the coal which may be used in the gasifying. Any suitable coal known to one of ordinary skill in the art may be used. The coal to be gasified may be provided in any suitable form, such as solid chunks, pellets, granules, powder, as a slurry in a suitable carrier, of any combination thereof. In preferred embodiments, the coal to be gasified is provided as a slurry in water. Such a slurry may have a weight ratio of coal to water of 50:50 to 95:5, preferably 55:45 to 90:10, preferably 60:40 to 80:20, preferably 65:35 to 75:25, preferably 70:30. In some embodiments, the gasifying is performed at 1200 to 1550° C., preferably 1225 to 1525° C., preferably 1250 to 1500° C., preferably 1275 to 1475° C., preferably 1300 to 1450° C., preferably 1325 to 1425° C., preferably 1350 to 1400° C., preferably 1360 to 1380° C., preferably 1365 to 1375° C., preferably 1370° C.

In some embodiments, the gasifying is performed at 45 to 67 bar, preferably 46 to 66 bar, preferably 48 to 64 bar, preferably 50 to 62 bar, preferably 52 to 60 bar, preferably 53 to 59 bar, preferably 54 to 58 bar, preferably 55 to 57 bar, preferably 56 bar.

At step 104, the method 100 includes transferring heat from the coal gas to a natural gas reforming mixture, including water and methane, thereby cooling the coal gas and heating the natural gas reforming mixture. It is important to note here that the heat transfer here does not involve a mass transfer. That is, there is no mixing of the coal gas and the natural gas reforming mixture. This heat transfer may be achieved through any suitable method or using any suitable equipment known to one of ordinary skill in the art. An example of such suitable equipment is a heat exchanger.

At step 106, the method 100 includes reforming the natural gas mixture to form a reformed natural gas, including hydrogen and carbon monoxide. The reforming may be steam reforming, also referred to as steam methane reforming when the natural gas mixture comprises mostly or consists primarily of methane (e.g. greater than 75%, or greater than 80% or greater than 85%, or greater than 90% methane by mole). In general, the reforming may be performed by any suitable method and using any suitable equipment known to one of ordinary skill in the art. The reforming involves conversion of hydrocarbons present in the natural gas mixture, for example methane, ethane, and propane, into a reformed natural gas which comprises hydrogen and carbon monoxide. The natural gas mixture may comprise hydrocarbons such as those listed above, and any other components that the skilled artisan would recognize as commonly associated with, included in, or act as impurities present in natural gas, such as sulfur containing impurities such as hydrogen sulfide and dimethyl sulfide, nitrogen, carbon dioxide, hydrogen, and noble gases such as helium and argon. The reformed natural gas may further comprise unreacted natural gas, such as methane, ethane, and propane, carbon dioxide, water vapor, and the other component gases listed above or oxidized versions thereof (e.g. sulfur dioxide, nitrogen oxides). In some embodiments, the natural gas mixture comprises at least 60% methane, preferably at least 65%, preferably at least 70%, preferably at least 75%, preferably at least 80%, preferably at least 85%, preferably at least 90% methane by mole, based on a total number of moles of natural gas mixture. The reforming may be performed with added water and/or oxygen. In some embodiments, the reforming is performed using a water to methane mole ratio ($H_2O:CH_4$) of 1:1 to 5:1, preferably 1.25:1 to 4.75:1, preferably 1.5:1 to 4.5:1, preferably 1.75:1 to 4.25:1, preferably 2:1 to 4:1, preferably 2.25:1 to 3.75:1, preferably 2.5:1 to 3.5:1, preferably 2.75:1 to 3.25:1, preferably 2.9:1 to 3.1:1, preferably 3:1. The reforming may involve the partial oxidation of methane. Examples of chemical reactions which may be performed during or associated with the natural gas reforming are given in Table 3 below. The reforming may be performed with the aid of a reforming catalyst. There is no specific limitation on the type or identity of reforming catalyst which may be used in the reforming. Any suitable reforming catalyst known to one of ordinary skill in the art may be used.

In some embodiments, the reforming is performed at 900 to 1200° C., preferably 910 to 1150° C., preferably 920 to 1100° C., preferably 930 to 1050° C., preferably 940 to 1000° C., preferably 950 to 975° C. In some embodiments the reforming is performed at 32 to 68 bar, preferably 36 to 66 bar, preferably 40 to 64 bar, preferably 44 to 62 bar, preferably 48 to 60 bar, preferably 52 to 58 bar, preferably 54 to 56 bar, preferably 55 bar.

At step 108, the method 100 includes mixing the coal gas, the reformed natural gas, and a recycled gas, including hydrogen and carbon monoxide, to form a synthesis gas. In some embodiments, the method 100 includes removing sulfur-containing species from the coal gas before mixing. In some embodiments, the synthesis gas has a hydrogen to carbon ratio of 45:55 to 55:45, preferably 48:52 to 54:46, preferably 49:51 to 53:47, preferably 50:49 to 52.5:47.5, preferably 50.5:49.5 to 52.0:48.0 preferably 50.75:49.25 to 51.75:48.25, preferably 51.0:49.0 to 51.5:48.5, preferably 51.1:48.9 to 51.2:48.8 by mole. In some embodiments, the synthesis gas has a high heating value (HHV) of 16.5 to 20.5 megajoules per kilogram (MJ/kg), preferably 17.0 to 20.25 MJ/kg, preferably 17.5 to 20.0 MJ/kg, preferably 18.0 to 19.75 MJ/kg, preferably 18.25 to 19.5 MJ/kg, preferably 18.5 to 19.25 MJ/kg, preferably 18.75 to 19.0 MJ/kg. In some embodiments, the method 100 includes removing sulfur-containing gases, particularly hydrogen sulfide, from the coal gas prior to mixing. In some embodiments, the method 100 includes removing sulfur-containing gases, particularly hydrogen sulfide, from the reformed natural gas prior to mixing. In general, the removal of sulfur-containing gases may be performed using any suitable method or with any suitable equipment known to one of ordinary skill in the art. In some embodiments, the removed sulfur-containing gases are transferred to a Claus plant for further processing. Preferably, after sulfur-containing gases removal, the coal gas, the reformed natural gas, or both are devoid of sulfur-containing species such as hydrogen sulfide, methanethiol, and dimethyl sulfide. Such sulfur-containing species may be detrimental to the method or system, for example by poisoning various catalysts used in certain steps of the method or by generating sulfuric acid or other acidic species which may cause catalyst poisoning, undesirable side reactions, and/or corrosion of the components of the system. Such removal is preferably specific to sulfur-containing species. That is, the removal does not also remove carbon monoxide or hydrogen from the synthesis gas.

In some embodiments, the method 100 includes removing carbon dioxide from the synthesis gas after mixing, but before reacting the synthesis gas to form methanol and the waste gas described below. In general, the removal of carbon dioxide may be performed using any suitable method or with any suitable equipment known to one of ordinary skill in the art. The presence of such carbon dioxide in the synthesis gas may be disadvantageous for the performance of the method or the system. For example, the presence of the carbon dioxide may cause undesirable side reactions or the generation of carbonic acid or other acidic species which may cause undesirable side reactions, corrosion of the components of the system, or the formation of carbonate materials which may interfere with the functioning of the system and even create hazardous conditions. Such removal is preferably specific to carbon dioxide. That is, the removal does not also remove carbon monoxide or hydrogen from the synthesis gas.

At step 110, the method 100 includes reacting the synthesis gas to form methanol and a waste gas, including water, carbon monoxide, and carbon dioxide. In general, the reacting (also referred to as methanol synthesis) may be performed by any suitable method and/or using any suitable equipment known to one of ordinary skill in the art. Typically, methanol synthesis is performed using or in the presence of a catalyst. There is no specific limitation on the type of identity of the catalyst which may be used. Any suitable methanol synthesis catalyst known to one of ordinary skill in the art may be used. In some embodiments, the reaction is performed at 125 to 275° C., preferably 150 to 250° C., preferably 160 to 240° C., preferably 170 to 230° C., preferably 175 to 225° C., 180 to 220° C., preferably 185 to 215° C., preferably 190 to 210° C., preferably 195 to 205° C., preferably 200° C. In some embodiments, the reaction is performed at 45 to 65 bar, preferably 46 to 64 bar, preferably 47 to 63 bar, preferably 48 to 62 bar, preferably 49 to 61 bar, preferably 50 to 60 bar, preferably 51 to 59 bar, preferably 52 to 58 bar, preferably 53 to 57 bar, preferably 54 to 56 bar, preferably 55 bar.

At step 112, the method 100 includes separating the methanol and the waste gas. In general, the separating may be performed by any suitable method or using any suitable equipment known to one of ordinary skill in the art. There is no specific limitation on the ways in which the separating may be performed. In some embodiments, the separating is performed with methanol in the gas phase. In such embodiments, the separating may be performed by any suitable technique for separating a mixture of gases. In some embodiments, the separating is performed with methanol in the liquid phase. In such embodiments, the separating may be performed using any suitable technique for separating a liquid and a gas or mixture of gases.

At step 114, the method 100 includes removing hydrogen from the waste gas to produce a dehydrogenated waste gas. In general, the separating may be performed by any suitable method or using any suitable equipment known to one of ordinary skill in the art. There is no specific limitation on the ways in which the separating may be performed. The separated hydrogen may be isolated, purified, or otherwise treated following the separating. The separated hydrogen may be used as in input in the syngas mixing to increase the hydrogen content of the synthesis gas.

At step 116, the method 100 includes subjecting the dehydrogenated waste gas to a water-gas shift reaction (WGSR) to produce the recycled gas. The recycled gas may comprise water, hydrogen, carbon dioxide, and carbon monoxide. In some embodiments, the recycled gas comprises 40 to 60 mol % hydrogen, 20 to 25 mol % carbon dioxide, 20 to 30 mol % water, and carbon monoxide and other impurity gases described above to balance. This recycled gas is delivered to the syngas mixer, and subsequently included in the synthesis gas. In some embodiments, prior to being delivered to the syngas mixer, water is separated from the recycled gas. In general, the separating may be performed by any suitable method or using any suitable equipment known to one of ordinary skill in the art. There is no specific limitation on the ways in which the separating may be performed. The separating may be performed with water in the gas phase or in the liquid phase. The inclusion of the recycled gas in the syngas mixture is particularly advantageous for reasons such as increasing the carbon conversion efficiency, increasing the energy efficiency (process efficiency), decrease production of waste materials such as carbon dioxide (e.g. $CO_2$ specific emissions), and/or increase the production of useful materials such as hydrogen.

In some embodiments, the method 110 has a carbon conversion efficiency of 32.5 to 47.5%, preferably 33.0 to 47.0%, preferably 33.5 to 46.5%, preferably 34.0 to 46.0%, preferably 34.5 to 45.5%, preferably 35.0 to 45.0%, preferably 35.5 to 44.5%, preferably 36.0 to 44.0%, preferably 36.5 to 43.5%, preferably 37.0 to 43.0%, preferably 37.25 to 42.5%, preferably 37.5 to 42.0%, preferably 37.75 to 41.5%, preferably 38.0 to 41.0%, preferably 38.25 to 40.75%, preferably 38.5 to 40.5%, preferably 38.75 to 40.25%, preferably 39 to 40%, preferably 39.25 to 39.75%, preferably 39.4%. In some embodiments, the method 110 has a production energy of 34 to 40 GJ/Mt total fuel, preferably 35.0 to 39.0 GJ/Mt total fuel, preferably 35.25 to 38.0 GJ/Mt total fuel, preferably 35.5 to 37.75 GJ/Mt total fuel, preferably 35.75 to 37.5 GJ/Mt total fuel, preferably 36.0 to 37.25 GJ/Mt total fuel, preferably 36.25 to 37.0 GJ/Mt total fuel, preferably 36.5 to 36.75 GJ/Mt total fuel, the total fuel being the sum of the methanol produced and hydrogen produced. In some embodiments, the method 110 has a process efficiency of 66 to 74%, preferably 66.5 to 73%, preferably 67 to 72%, preferably 67.5 to 71.5%, preferably 68 to 71%, preferably 68.25 to 70.75%, preferably 68.5 to 70.5%, preferably 68.75 to 70.25%, preferably 69.0 to 70.0%, preferably 69.25 to 69.75%, preferably 69.3 to 69.5%, preferably 69.4%, the process efficiency calculated by:

$$\text{Process Efficiency}(\eta net) = \frac{\text{Methanol thermal energy }[MWth] + \text{H2 thermal energy }[MWth]}{\text{Feed stock thermal energy }[MWth] + \text{Energy consumed }[MWth]} \times 100$$

Figure 2:
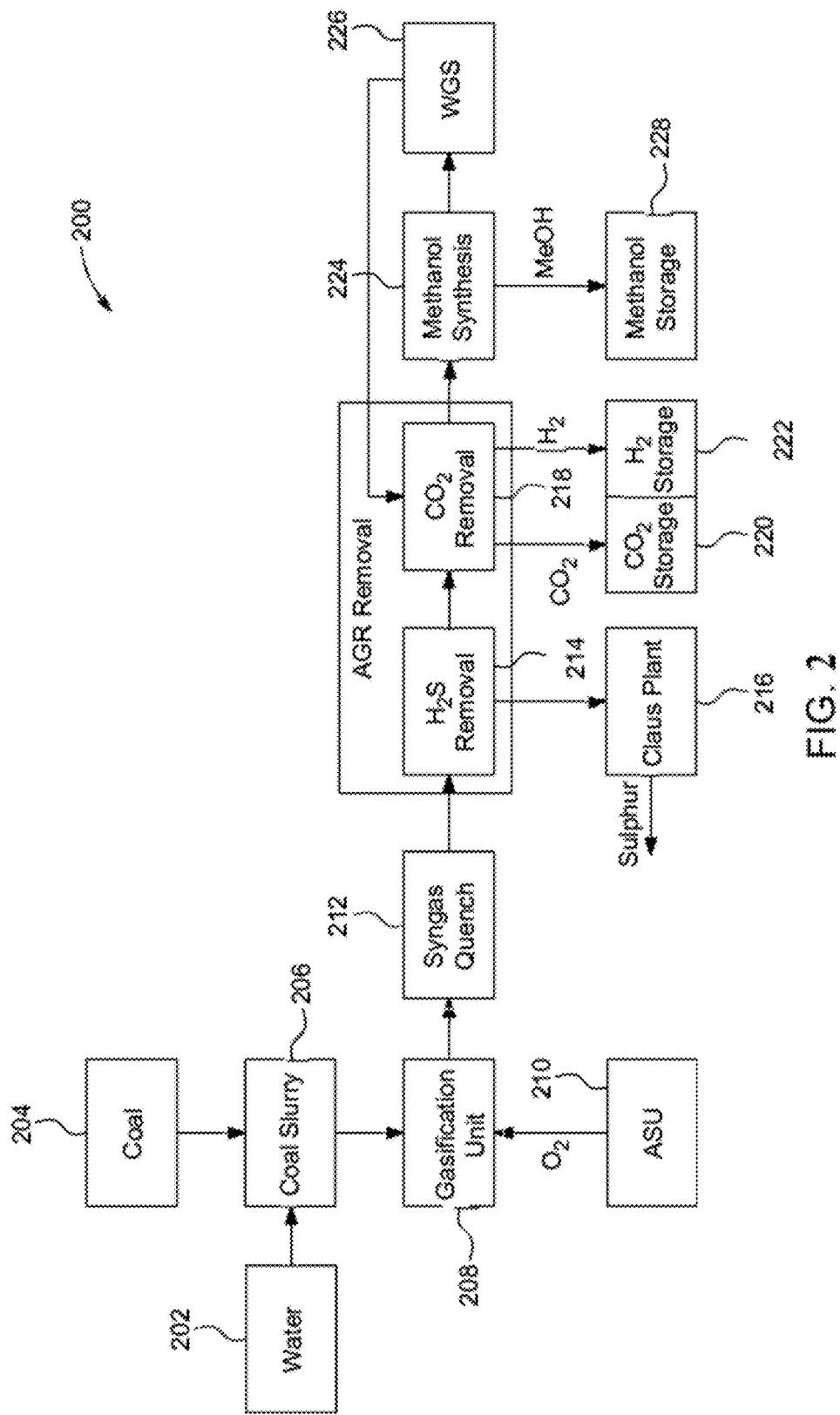
FIG. 2 illustrates components of the CTM and hydrogen production process with $CO_2$ capture, according to certain embodiments.

Referring to FIG. 2, a system block diagram 200 for methanol production according to case 1 descried in the examples below is illustrated. It is included here primarily for the purposes of comparison, further expand upon in the examples below. In case 1, the coal water slurry 206 is produced using the water carrier component 202 and the finely granulated coal 204. The coal water slurry 306 is fed to the gasification unit 208 where it is partially oxidized with the oxygen produced from an air separation unit (ASU) 210, followed by additional steam to generate synthesis gas. The temperature of the synthesis gas is then decreased in the radiant and synthesis gas quenching units (Syngas Quench) 212. The method further includes removal of acid gases ($H_2S$) 214 and $CO_2$ 218 from the synthesis gas. Collectively this step is known as acid gas removal (AGR) removal. The $H_2S$ from the AGR unit may be further treated in the Claus plant 216 to recover the elemental sulfur. The synthesis gas is then used in methanol synthesis unit 224. After the synthesis, the methanol is separated. The unreacted synthesis gas from the methanol synthesis reactor is further fed into the WGS unit 226, where the CO in the synthesis gas reacts with the steam to generate $H_2$ and $CO_2$. The outlet stream of the WGS unit 226 containing $H_2$ and $CO_2$ is recycled back to the AGR unit where a solvent and $H_2$ absorbed the $CO_2$ was separated from the process, which is sent to the storage section of $CO_2$ 320 and $H_2$ 222. The system of FIG. 2 lacks the natural gas reforming and related heat integration present in the system of the present disclosure.

Figure 3:
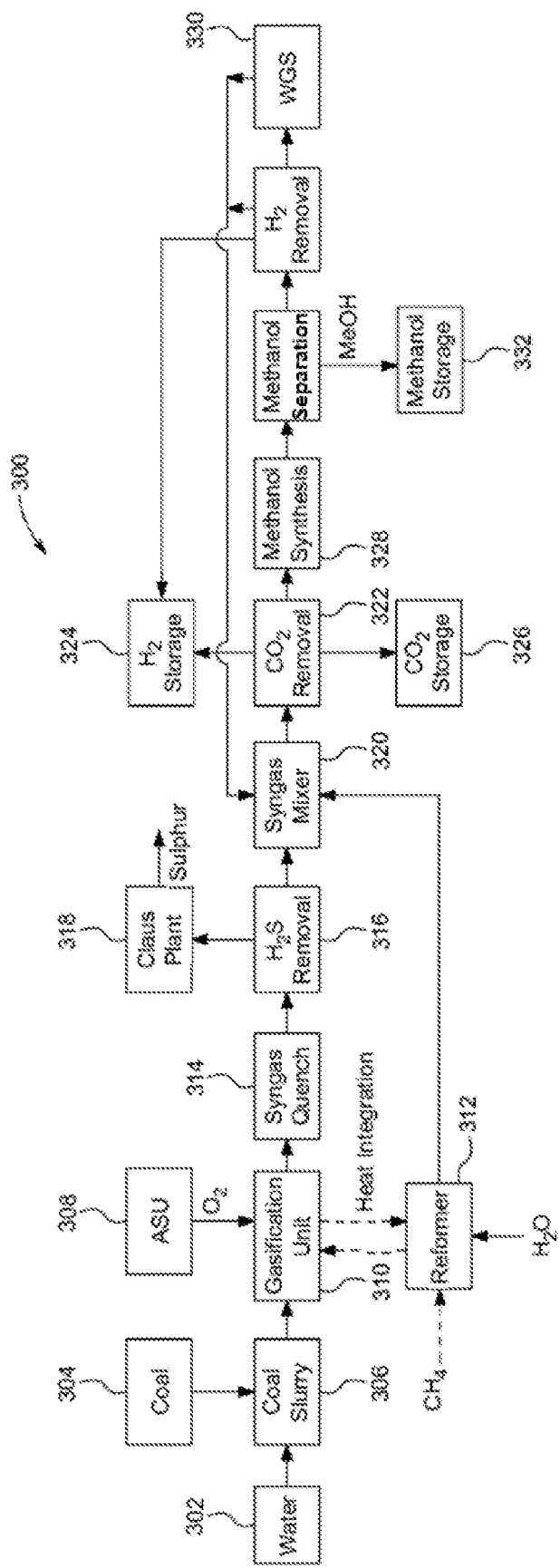
FIG. 3 illustrates components of the integration of a coal gasification and natural gas reforming models for dual methanol and hydrogen production with carbon dioxide ($CO_2$) capture, according to certain embodiments.

Referring to FIG. 3, a system block diagram 300 for methanol production according to the present disclosure is illustrated. FIG. 3 represents the model system and additional steps to refine the process referred to as case 2 in the examples below. The case 2 process model describes the proposed system, using natural gas and coal feedstocks as shown in the FIG. 3. In case 2, the natural gas reforming model is integrated with the coal gasification model to enhance the synthesis gas production potential, allowing for utilization of the heat from the coal-derived synthesis gas into the natural gas reformer without incurring any additional energy penalties as well as increasing the efficiency through the generation and use of the recycled gas in the syngas mix. In FIG. 3, the reformer unit 312 is present in the parallel system configuration and has heat integration with the coal gasifier as described above. The synthesis gas is cooled in the radiant and convective heat exchangers herein referred to as Syngas Quench 314, followed by $H_2S$ removal 316 and may be transferred to Claus plant 318. The coal gasifier-derived synthesis gas is then mixed with the reformed natural gas in the Syngas mixer 320, followed by the $CO_2$ removal in the acid gas removal units where $H_2$ 324 and $CO_2$ 326 are stored separately. The synthesis gas is then fed to the methanol production unit for methanol synthesis 328. Following separation, the unreacted synthesis gas is provided to the WGS unit 330 to react the CO and the steam to generate $H_2$ and $CO_2$ as described in the case 1. The placement of WGS reactors at the outlet of methanol synthesis reactors allowed the conversion of unreacted synthesis gas into hydrogen and $CO_2$, followed by $CO_2$ removal 322 while obtaining pure hydrogen and methanol, which is stored in a methanol storage unit 332.

The examples below are intended to further illustrate protocols for the construction and operation of the system and for performing the method of the present disclosure and are not intended to limit the scope of the claims.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

EXAMPLES

System Basis and Simulation Methodology

The process models are developed in Aspen Plus® V11, where Peng-Robinson with Boston-Mathias alpha function (PR-BM) was selected as an effective thermodynamic package. Table 1 highlights some of the system assumptions for the system of major unit processes. Coal is an un-conventional component because of its in-consistent composition and is mainly defined based on proximate, ultimate, and heating value information, as represented in Table 2 [T. Fout, A. Zoelle, D. Keairns, M. Turner, M. Woods, N. Kuehn, et al. Cost and performance baseline for fossil energy plants volume 1b: bituminous coal (IGCC) to electricity revision 2b—year dollar update. United States Department of Energy: Washington, D.C., USA. (2015), incorporated herein by reference in its entirety]. Methanol and hydrogen synthesis processes involve a sub-process: coal gasification, natural gas reforming, synthesis gas cleaning, acid gas removal (AGR), a heat exchanger network (HEN), and methanol synthesis. Table 3 represents some of the key reactions involved in coal gasification, the natural gas reforming, water gas shift (WGS) reaction, Claus plant, and methanol synthesis reactors. Similarly, the system specifications and operational parameters used in Aspen Plus for modeling each unit process are provided in Table 4. For instance, the RYield model was used to determine the yield of the coal-based composition, which further converts the coal into its constituent elements. RGibbs reactor model was used for both the coal gasification and the natural gas reforming processes which functions on the principle of minimizing Gibbs free energy to generate reaction products which is usually the synthesis gas in both the processes. To develop the AGR units for the removal of $CO_2$ and $H_2S$ from the synthesis gas, RadFrac modules were used where the tolerable limits of $CO_2$ and $H_2S$ are specified to achieve the required purity. For the development of WGS, REquil reactor models were used due to the known stoichiometry between the reactants and products at the specified temperatures. The methanol synthesis reactions were usually carried out over copper/zinc oxide/aluminium oxide (Cu/ZnO/$Al_2O_3$) based catalyst, where RPlug reactor model was used in the simulation. The methanol synthesis reactions mainly involve the reactions between CO and $H_2$, where a reverse water gas (RWGS) also occurred simultaneously to produce methanol and synthesis gas as shown in the equations provided in Table 3. The rate of reactions and equilibrium constants in the methanol production may be calculated using equations. (1)-(4).

$$r_{CH3OH} = \frac{k_1 P_{CO2} P_{H2}\left[1 - \left(\frac{1}{K_1^{eq}}\right)\left(\frac{P_{H20} P_{CH30H}}{P_{H2}^3 P_{CO2}}\right)\right]}{\left(1 + K_3\left(\frac{P_{H20}}{P_{H2}}\right) + K_4\sqrt{P_{H2}} + K_5 P_{H20}\right)^3} \quad (1)$$

$$r_{RWGS} = \frac{k_2 P_{CO2}\left[1 - K_2^{eq}\left(\frac{P_{H20} P_{CO}}{P_{H2}^3 P_{CO2}}\right)\right]}{\left(1 + K_3\left(\frac{P_{H20}}{P_{H2}}\right) + K_4\sqrt{P_{H2}} + K_5 P_{H20}\right)^3} \quad (2)$$

$$\log_{10} K_1^{eq} = \frac{3066}{T} - 10.592 \quad (3)$$

$$\log_{10} 1/K_2^{eq} = \frac{-2073}{T} - 2.029 \quad (4)$$

TABLE 1

System assumptions for model development

| Unit/Component/System | Modelling Unit | Parameter |
|---|---|---|
| Gasification Reactor | RGibbs (Reactor) | Coal flow rate = 62.01 kg/s Temp/Press: 1350-1370° C./56 bar |
| Reformer | Gibbs (Reactor) | NG flow rate: 5.5 kg/sec $H_2O$:$CH_4$ = 3:1 Temp/Press: 900° C./32 bar |
| Air Separation Unit (ASU) | HeatX, Compr | Oxygen Purity 95% (vol) |
| Methanol Reactor | RGibbs (Reactor) | Cu based catalyst Pressure/Temp: 55 bar/200° C. |

TABLE 2

Coal and natural gas composition.

| Coal composition and analysis | Weight percentage (%) |
|---|---|
| Fixed carbon | 44.19 |
| Volatile matter | 34.99 |
| Ash | 9.7 |
| Moisture | 11.12 |
| Sulphur | 2.51 |
| Total | 100 |
| Lower Heating Value (LHV) | 26151 kj/kg (Btu/lb) |
| Ultimate Analysis | As Received (weight %) |
| Moisture | 11.12 |
| Oxygen | 6.88 |
| Hydrogen | 4.5 |
| Nitrogen | 1.25 |
| Chlorine | 0.29 |
| Sulphur | 2.51 |

TABLE 2-continued

Coal and natural gas composition.

| Ash | 9.7 |
|---|---|
| Carbon | 63.75 |
| Total | 100 |
| Natural Gas Composition | |
| $CH_4$ | 0.939 |
| $CO_2$ | 0.01 |
| $N_2$ | 0.008 |
| $C_4H_{10}$ | 0.004 |
| $C_3H_8$ | 0.007 |
| $C_2H_6$ | 0.032 |
| Total | 1 |
| LHV | 47.76 MJ/kg |

TABLE 3

Chemical reactions involved in the process
Chemical reactions involved in the process.

| Gasification reactor | |
|---|---|
| $C_{(s)} + H_2O \leftrightarrow CO + H_2$ | $\Delta H = +131.4$ MJ/kmol |
| $C_{(s)} + CO_2 \leftrightarrow 2\,CO$ | $\Delta H = +172.6$ MJ/kmol |
| $C_{(s)} + \frac{1}{2}O_2 \rightarrow CO$ | $\Delta H = -111$ MJ/kmol |
| $C_{(s)} + 2H_2 \rightarrow CH_4$ | $\Delta H = -75$ MJ/kmol |
| $CO + \frac{1}{2}O_2 \rightarrow CO_2$ | $\Delta H = -283$ MJ/kmol |
| $CH_4 + H_2O \leftrightarrow 3H_2 + CO$ | $\Delta H = -41$ MJ/kmole |
| $C_{(s)} + O_2 \rightarrow CO_2$ | $\Delta H = -409$ MJ/kmol |
| $H_2 + \frac{1}{2}O_2 \rightarrow H_2O$ | $\Delta H = +206$ MJ/kmol |
| Water Gas Shift Reactors | |
| $CO + H_2O \rightarrow H_2 + CO_2$ | $\Delta H = -41$ MJ/kmole |
| Steam Methane Reforming Reactor | |
| $3C_2H_6 + H_2O \rightarrow 5CH_4 + CO$ | $\Delta H = +3.6460$ MJ/kmol |
| $3C_3H_8 + 2H_2O \rightarrow 7CH_4 + 2CO$ | $\Delta H = +16.607$ MJ/kmol |
| $3C_4H_{10} + 3H_2O \rightarrow 9CH_4 + 3CO$ | $\Delta H = +41.116$ MJ/kmol |
| $CH_4 + 2O_2 \rightarrow CO_2 + 2H_2O$ | $\Delta H = -802.54$ MJ/kmol |
| $CH_4 + H_2O \rightarrow CO + 3H_2$ | $\Delta H = +206.12$ MJ/kmol |
| Methanol Reactor | |
| $CO + 2H_2 \leftrightarrow CH_3OH$ | $\Delta H = -90.55$ MJ/kmol |
| $CO_2 + 3H_2 \leftrightarrow CH_3OH + H_2O$ | $\Delta H = -49.43$ MJ/kmol |
| $CO_2 + H_2 \leftrightarrow CO + H_2O$ | $\Delta H = 41.12$ MJ/kmol |
| Claus plant | |
| $H_2S + 3/2O_2 \rightarrow H_2O + SO_2$ | $\Delta H = -560$ MJ/kmol |
| $2H_2S + SO_2 \rightarrow 2H_2O + 3S$ | $\Delta H = -41.8$ MJ/kmol |
| $2H_2S + 3O_2 \rightarrow 2H_2O + 2SO_2$ | $\Delta H = -518$ MJ/kmol |

TABLE 4

Process System Assumptions and Specifications.
Process System Assumptions and Specifications.

| Equipment | Description | Aspen Model |
|---|---|---|
| Air Separation Unit (ASU) | Oxygen flowrate = 50.57 kg/sec Temp/Pressure = 90.9° C./6.76 Mpa $O_2$ Purity = 95% (mole %) Energy Requirement: 0.25 kWh/kg | Separator, Multi-Stage compressor |
| Gasification Unit | Temp/Pressure = 1370° C./5.6 Mpa Carbon conversion = 98% Coal flow rate = 62.20 kg/sec Coal and water slurry ratio (wt) = 70:30 | RYield, RGibbs (Reactor) |
| Natural Gas Reforming Unit | Natural gas flowrate = 5.5 kg/sec Temp/Pressure = 950° C./5.5 Mpa $H_2O$/$CH_4$ ratio = 3.0 Nickel based catalyst | RGibbs (Reactor) |

TABLE 4-continued

Process System Assumptions and Specifications.
Process System Assumptions and Specifications.

| Equipment | Description | Aspen Model |
|---|---|---|
| Water gas Shift Conversion (WGS) | Sour Catalyst (Co—Mo) 2 Adiabatic reactors Steam/CO: ~2.2 CO conversion~99% | REquil Reactor |
| AGR Unit | Rectisol Process (Methanol Solvent) Temp/Pressure = −33° C./5.5 Mpa $H_2S$ Removal = 100 ppbv $CO_2$ Removal = 90% | Flash, RadFrac |
| Methanol Reactor | Temp/Pressure = 200° C./5.5 Mpa Cu/ZnO/$Al_2O_3$ based catalyst | RPlug (Reactor) |
| Claus plant | Oxygen blown type | RStoic, HeatX |
| Heat Exchangers | ΔTmin = 10° C. | Heater, HeatX, MHeatX |

Validation of Process Models

The validation of the developed process is also important to evaluate the reliability of the model before doing any further analysis. To validate the process models, some of the important process-units (ASU, coal gasification and natural gas reforming) were selected where the composition of the synthesis gas at the outlet, of the ASU, the coal gasification, and the natural gas reforming units, was compared with the literature [Ahmed U, Kim C, Zahid U, Lee C-J, Han C. Integration of IGCC and methane reforming process for power generation with CO2 capture. Chem Eng Process Process Intensif 2017; 111:14-24; Field R P, Brasington R. Baseline flowsheet model for IGCC with carbon capture. Ind Eng Chem Res 2011; 50:11306-12; and P. N. Panahi, S. M. Mousavi, A. Niaei, A. Farzi, D. Salari. Simulation of methanol synthesis from synthesis gas in fixed bed catalytic reactor using mathematical modeling and neural networks. Int J Sci Eng Res. 3 (2012) 162-8, each of which is incorporated herein by reference in its entirety]. Table 5 represents the composition of the outlet streams of each specific unit along with the error percentage in the results. The models were initially developed according to the temperature, pressure and stream compositions provided in the literature and the results were benchmarked with the simulation results. It may be observed from results that the relative error between simulation and literature values for the synthesis gas composition was below 2% which is acceptable for conducting the simulation-based process integration studies. However, the integration of these processes in the developed models may result in different synthesis gas composition due to the change in inlet stream compositions and operational conditions required by the process.

TABLE 5

Validation of Models.
Validation of Models.

| Parameter | Literature values | Simulation | Error % |
|---|---|---|---|
| Air Separation Unit | | | |
| T [° C.] | 91 | 91 | — |
| P [Mpa] | 6.8 | 6.8 | — |
| $O_2$ | 94.90% | 94.97% | −0.07% |
| $N_2$ | 1.88% | 1.88% | 0.00% |
| Ar | 3.22% | 3.15% | 0.07% |
| Gasifier | | | |
| T [° C.] | 1370.0 | 1370.0 | — |
| P [Mpa] | 5.6 | 5.6 | — |
| CO | 0.389 | 0.393 | −0.004 |
| $CO_2$ | 0.105 | 0.100 | 0.005 |
| $H_2$ | 0.294 | 0.301 | −0.007 |
| $H_2O$ | 0.186 | 0.181 | 0.006 |
| $CH_4$ | 0.000 | 0.000 | 0.000 |
| $H_2S$ | 0.007 | 0.007 | 0.000 |
| $N_2$ | 0.009 | 0.009 | 0.000 |
| Others | 0.009 | 0.009 | 0.000 |
| Reformer | | | |
| T [° C.] | 1040 | 1040 | — |
| P [Mpa] | 3.2 | 3.2 | — |
| CO | 0.470 | 0.456 | 0.014 |
| $CO_2$ | 0.060 | 0.054 | 0.006 |
| $H_2$ | 0.380 | 0.373 | 0.007 |
| $H_2O$ | 0.070 | 0.080 | −0.010 |
| CH4 | 0.010 | 0.018 | −0.008 |
| Others | 0.010 | 0.019 | −0.009 |

Technical Process Performance Indicators

To analyze and compare the process performance of both the cases, some of the key technical indicators used are as follows:

i) Process Efficiency

The overall process performance in terms of process efficiency was calculated on the basis of heating value of fuel ($H_2$ and methanol) produced from the process divide by the feedstock heating value and the energy consumed in the process as shown in Equation. (5)

$$\text{Process Efficiency}(\eta net) = \frac{\text{Methanol thermal energy } [MWth] + H_2 \text{ thermal energy } [MWth]}{\text{Feed stock thermal energy } [MWth] + \text{Energy consumed } [MWth]} \times 100\% \quad (5)$$

ii) Carbon Conversion Efficiency

The carbon conversion efficiency represents the total carbon present in the feedstocks to its conversion into the methanol as represented in the Equation. (6), where the $C_{MeOH}$ represents the flow rate of methanol kilograms per second (kg/s) and $C_{feedstock}$ represents the total carbon in the feedstock (kg/s).

$$\eta_C = \frac{C_{MeOH}}{C_{feedstock}} \times 100\% \quad (6)$$

iii) $CO_2$ Specific Emission $CO_2$ specific emissions is an important environmental quality control indicator showing the un-captured $CO_2$ from any process. The Equation. (7) represents the uncaptured $CO_2$ from the process for each unit of fuel produced.

$$CO_2 \text{ specific emissions} = \frac{CO_2 \text{Emissions}\left(\frac{kmol}{hr}\right)}{\text{Methanol Production} + H_2 \text{Production}\left(\frac{kmol}{hr}\right)} \quad (7)$$

Comparative Study of Case 1 and Case 2

Figure 4:
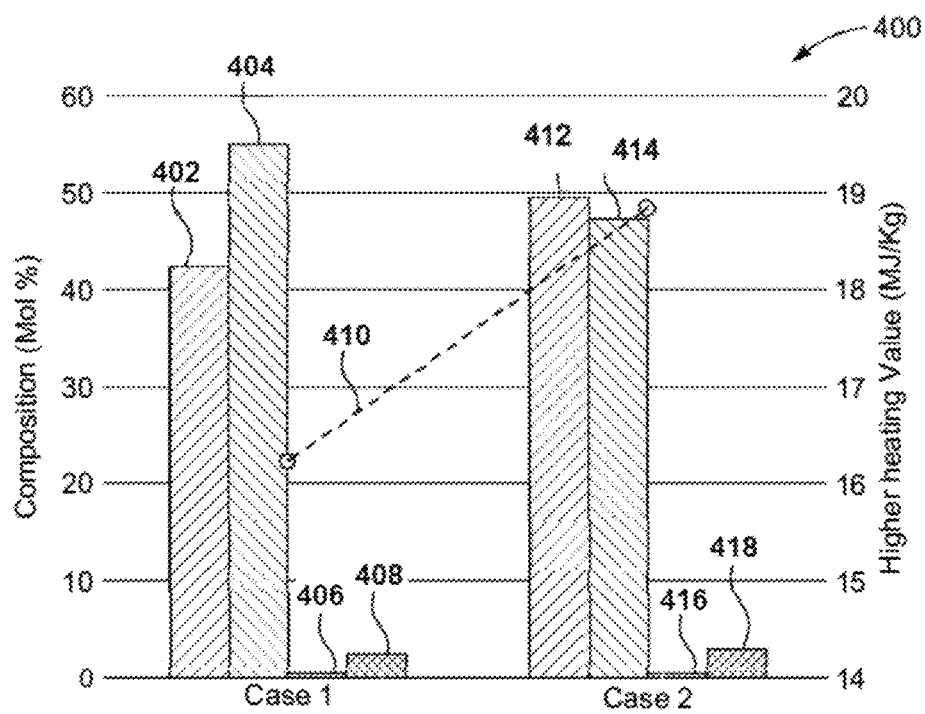
FIG. 4 is a graphical representation of a synthesis gas composition and higher heating value (HHV) at the inlet of the methanol reactor, according to certain embodiments.
Figure 5:
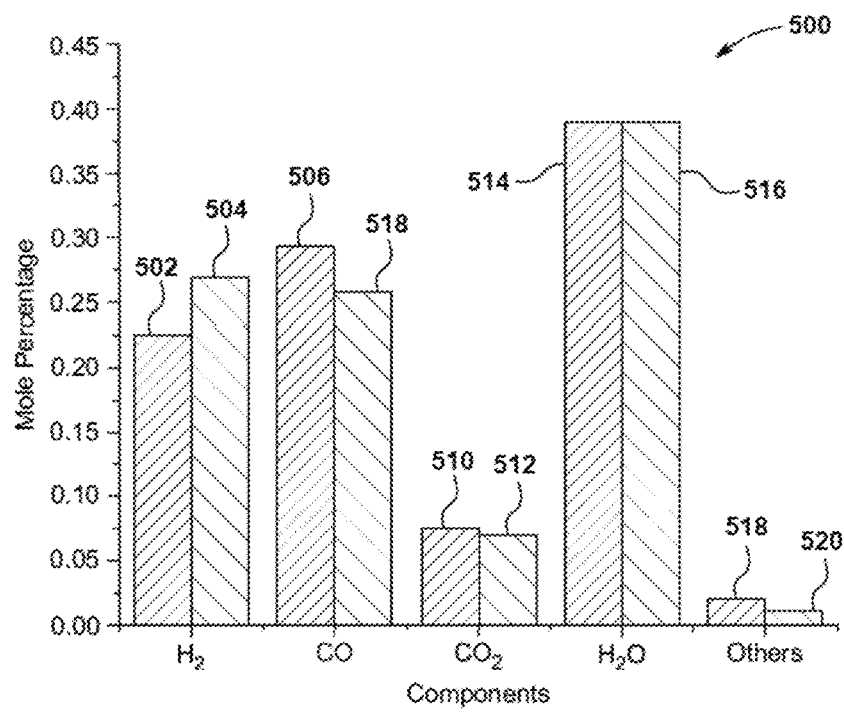
FIG. 5 is a graphical representation of the synthesis gas composition at an inlet of a methanol reactor, according to certain embodiments.

Case 1 was modeled as the conventional CTM process where the syngas' cold gas efficiency (CGE) is based on the gasifier operational conditions, type of feed, and the heat integration network. Case 1 was then retrofitted with a steam methane reforming (SMR) technology to generate case 2 to utilize the key technical benefits of both the gasification and reforming technologies. The retrofitting of the SMR unit in the parallel system configuration allowed to use the high enthalpy heat from the gasifier derived synthesis gas but also helped in increasing the hydrogen to carbon ratio (HCR) ratio at the inlet of the methanol reactor. In both cases, 62.19 kg/s of the bituminous coal has been used as a feedstock for the gasification unit. Unlike case 1, case 2 consumes an additional natural gas at the rate of 5.5 kg/s in the reforming unit. The coal to natural gas ratio of 5.5:1 is maintained in case 2 to utilize maximum heat from the gasification unit for the reforming of natural gas without any additional heat supply. The results showed that a significant increase in syngas production capacity was observed in case 2 compared to case 1. The HCR obtained in case 2 is also higher than case 1. FIG. 4 shows the results 400 of synthesis gas composition at the inlet of the methanol reactor for case 1 and case 2, respectively. The gas found at the inlet of the methanol reactor are $H_2$, CO, $CO_2$, and other gases. The $H_2$ composition at the inlet of the methanol reactor in case 1 402 and case 2 404 respectively are about 42% and 65% respectively. Similarly, 406, 412 and 416 show the CO, $CO_2$ and other gases in case 1 respectively, whereas 408, 414 and 418 show the CO, $CO_2$ and other gases in case 2, respectively. From the graph 400, it can be observed that the percentage of $H_2$ is significantly higher in case 2 when compared to case 1, while percentage levels of CO, $CO_2$ and other gases was found to be comparable for both case 1 and case 2, respectively. The HHV associated with samples from case 1 and case 2 is represented by 410. In another embodiment, FIG. 5 shows the results 500 of synthesis gas composition at the inlet of the methanol reactor for case 1 and case 2 in different compositions. 502 and 504 show the $H_2$ composition in case 1 and case 2 respectively. Similarly, 506, 510, 514 and 518 show the CO, $CO_2$, $H_2O$ and other gases in case 1 respectively, whereas 508, 512, 516 and 520 show the CO, $CO_2$, $H_2O$ and other gases in case 2, respectively.

To ensure the unbiased analysis, the process performance indicator for calculating the overall process efficiency has been used in equation 8. The overall energy efficiency is a function of heat input rates in the form of thermal energy and the heating value of the produced methanol along with the power generation potential for each case.

$$\text{Energy Efficiency} = \frac{\text{Produced electricity} + \text{Heat of Produced MeOH}}{\text{Feed stock heating value} + \text{Energy Consumed}} \% \quad (8)$$

Figure 6:
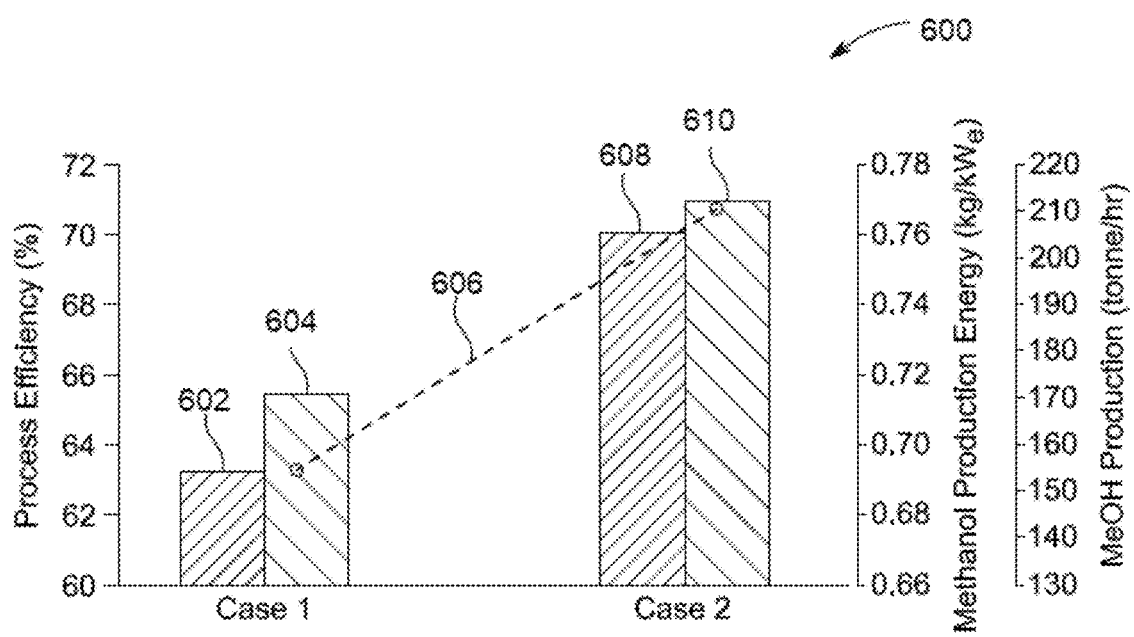
FIG. 6 is a graphical representation of a comparison of the methanol production rates and energy for a case 1 system and a case 2 system, according to certain embodiments.

The results showed that the process efficiency calculated for case 1 and case 2 is 63% and 70%, respectively. The heat generated from both cases was utilized for electricity generation using the steam turbine cycle. The results showed that the electricity generation potential from case 1 and case 2 is calculated as 11.26 megawatt electrical (MWe) and 16.70 MWe, respectively. The methanol production capacity and energy requirement from a specific fuel are important criterion to analyze the process's technical and economic feasibility. It may be observed that the difference in the process configuration and the heat exchanger network highly affects the overall production capacity. The simulation results showed that the methanol production capacity from case 1 and case 2 is calculated as 171 mega tonnes per hour (MT/hr.) and 212 MT/hr, respectively, where case 2 shows 24% higher methanol production capacity compared to case 1. FIG. 6 also represents the results 600 of comparison between two cases in terms of process efficiency (%). The process efficiency is represented by 602 and 604 for case 1, and case 2 respectively. It can be observed that the process efficiency for case 2 was found to be about 20% higher than case 1. Similarly, the methanol production was estimated for both case 1 608 and case 2 610, and it can be observed from the graph that the methanol production was found to be higher with case 2 than with case 1. The results showed that the specific methanol production for case 1 604 and case 2 610 is calculated as 0.7 kilograms per watt (kg/watt) and 0.8 kg/watt, respectively. The methanol production efficiency is depicted by 606.

Figure 7:
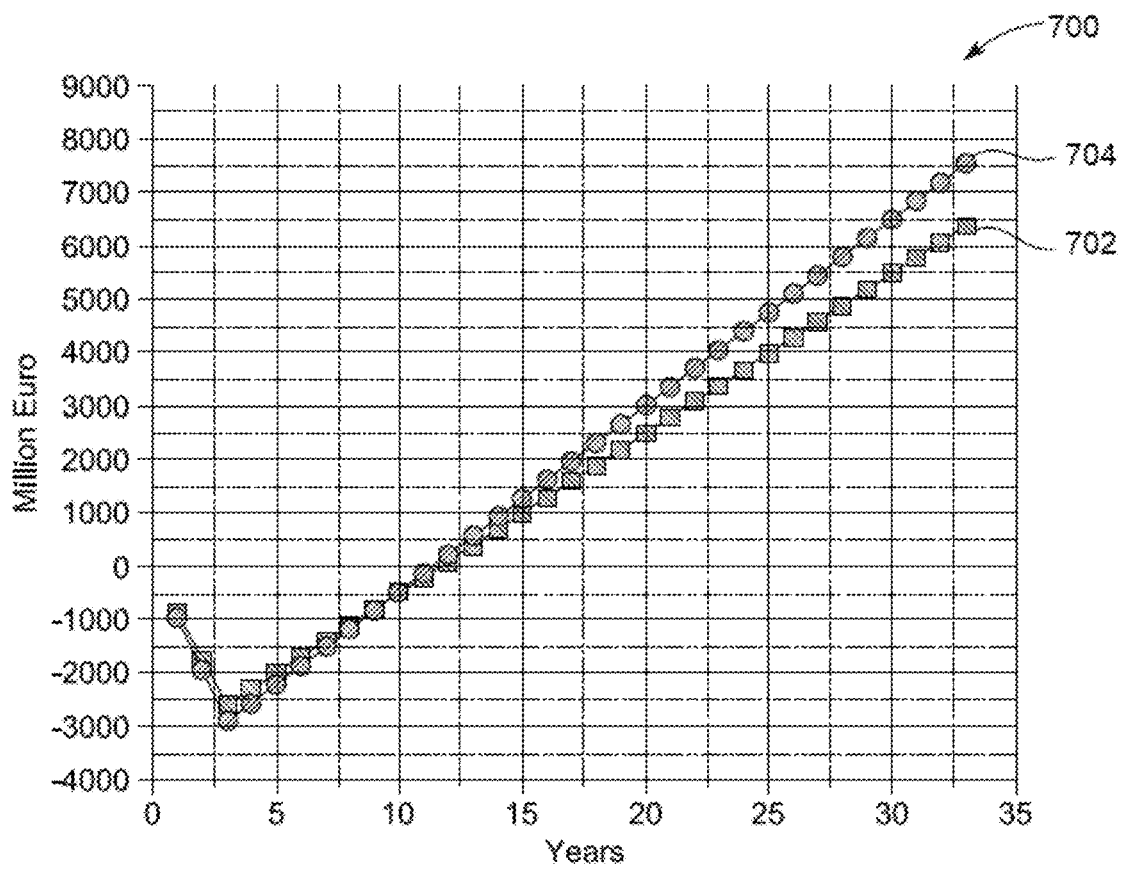
FIG. 7 illustrates cumulative cash flow for the case 1 system and the case 2 system, according to certain embodiments.

FIG. 7 represents the cumulative economic assessment results 700 for both case 1 702 and case 2 704 system where the project's lifetime is assumed to be 33 years. It has been analyzed from the results that the payback time for both case 1 702 and case 2 704 is calculated as 11 years, where case 2 704 showed a higher overall monetary production of 2600-2700 million euros (M€) as compared to case 1 702 throughout the lifetime of the project.

Methanol and $H_2$ Production Rates and Overall Process Performance

Two process models (case 1 and case 2) were developed and compared for the dual production of methanol and hydrogen. Case 1 is based on the conventional coal to the methanol production process where slight modifications have been done for co-production of hydrogen from the process as discussed in the FIG. 3. Case 2 is an updated version of case 1 where the natural gas reforming model was integrated with the gasification model to utilize the high enthalpy heat from the gasifier derived synthesis gas and minimizing the energy penalties for the reforming unit. This integration significantly increased the synthesis gas production while increasing the HCR in the synthesis gas. FIG. 5 represents the synthesis gas composition at the inlet of the methanol synthesis unit to see the impact of integrating the reforming unit in case 2 and its comparison with case 1.

The results showed that case 2 offers higher HCR in the synthesis gas compared to the case 1. Moreover, the HHV of the synthesis gas has been increased due to an increase in the $H_2$ concentration in the synthesis gas for case 2. The HHV of the synthesis gas was calculated as 16.24 megajoules per kilogram (MJ/kg) and 18.84 MJ/kg for case 1 and case 2, respectively. The HCR in the synthesis gas, and the heating value, highly affects the net methanol and $H_2$ production rates. For instance, methanol and $H_2$ production rates for case 1 have been calculated as 30.71 kg/s and 3.15 kg/s, respectively. Similarly, case 2 offers the methanol and $H_2$ production rates of 44.77 kg/s and 2.62 kg/s, respectively. Tables 6A-6B highlight the stream composition and flow rates at the outlet of all the significant processes involved in the case 1 and case 2.

TABLE 6A

Composition of process streams and flow rates.

| | Coal Case1/Case2 | ASU Case1/Case2 | Gasifier Case1/Case2 | Reformer Case 1 | Reformer Case 2 | AGR Unit Case 1 | AGR Unit Case 2 |
|---|---|---|---|---|---|---|---|
| T [°C] | 60 | 91 | 1370 | — | 947 | 200 | 200 |
| P [MPa] | 7200 | 6800 | 5600 | — | 5500 | 5500 | 5500 |
| Mass Flow (kg/s) | 62.20 | 50.57 | 138.65 | — | 23.22 | 78.99 | 86.99 |
| Mass % | | | | | | | |
| $H_2$ | — | — | 2.87% | — | 7.78% | 5.01% | 6.62% |
| CO | — | — | 52.02% | — | 22.70% | 90.26% | 87.98% |
| $CO_2$ | — | — | 20.84% | — | 16.91% | 0.30% | 0.31% |
| $H_2O$ | — | — | 15.38% | — | 48.37% | — | — |
| $O_2$ | — | 94.46% | — | — | — | — | — |
| $CH_4$ | — | — | 0.01% | — | 3.92% | 0.02% | 1.01% |
| $N_2$ | — | 1.63% | 1.16% | — | 0.31% | 1.98% | 1.88% |
| Ar | — | 3.91% | 1.43% | — | — | 2.41% | 2.19% |
| $CH_3OH$ | — | — | — | — | — | — | — |
| Others | — | — | 6.29% | — | 0.02% | 0.01% | 0.01% |
| Mole Flow (kmol/s) | — | 1.57 | 6.55 | — | 1.86 | 4.62 | 5.76 |
| Mol % | | | | | | | |
| $H_2$ | — | — | 30.12% | — | 48.28% | 42.52% | 49.63% |
| CO | — | — | 39.31% | — | 10.14% | 55.10% | 47.46% |
| $CO_2$ | — | — | 10.02% | — | 4.81% | 0.12% | 0.11% |
| $H_2O$ | — | — | 18.07% | — | 33.58% | 0.00% | 0.00% |
| $O_2$ | — | 94.97% | — | — | — | — | — |
| $CH_4$ | — | — | 0.02% | — | 3.05% | — | — |
| $N_2$ | — | 1.88% | 0.87% | — | 0.14% | 1.21% | 1.02% |
| Ar | — | 3.15% | 0.76% | — | — | 1.03% | 0.83% |
| $CH_3OH$ | — | — | — | — | — | — | — |
| Others | — | 0.00% | 0.82% | — | 0.01% | 0.03% | 0.95% |

TABLE 6B

Composition of process streams and flow rates.

| | Methanol Synthesis Case 1 | Methanol Synthesis Case 2 | WGS Outlet Case 1 | WGS Outlet Case 2 | $H_2$ Production Case 1 | $H_2$ Production Case 2 | $CO_2$ Storage Case 1 | $CO_2$ Storage Case 2 |
|---|---|---|---|---|---|---|---|---|
| T [°C] | 35 | 35 | 150 | 150 | 25 | 25 | 25 | 25 |
| P [MPa] | 100 | 100 | 5500 | 5500 | 100 | 100 | 100 | 100 |
| Mass Flow (kg/s) | 31.1 | 45.22 | 71.49 | 60.36 | 4.78 | 3.97 | 90.06 | 83.46 |
| Mass % | | | | | | | | |
| $H_2$ | — | — | 6.30% | 6.12% | 94.00% | 93.00% | 0.01% | 0.11% |
| CO | — | — | 0.04% | 0.05% | — | — | — | — |
| $CO_2$ | — | — | 62.25% | 61.64% | 3.00% | 4.00% | 96.64% | 96.29% |
| $H_2O$ | — | — | 28.04% | 27.28% | 2.00% | 2.00% | 1.67% | 1.68% |
| $O_2$ | — | — | — | — | — | — | — | — |
| $CH_4$ | — | — | 0.01% | 0.92% | — | — | — | — |
| $N_2$ | — | — | 1.43% | 1.75% | — | — | 1.68% | 1.82% |
| Ar | — | — | 1.72% | 2.03% | — | — | — | — |
| $CH_3OH$ | 99.00% | 99.00% | — | — | — | — | — | — |
| Others | 1.00% | 1.00% | 0.21% | 0.21% | 1.00% | 1.00% | 0.25% | 0.11% |
| Mole Flow (kmol/s) | 0.97 | 1.41 | 4.43 | 3.69 | 1.59 | 1.32 | 2.13 | 1.97 |
| Mol % | | | | | | | | |
| $H_2$ | — | — | 50.41% | 49.53% | 97.00% | 97.00% | 0.20% | 0.25% |
| CO | — | — | 0.02% | 0.03% | — | — | — | — |
| $CO_2$ | — | — | 22.82% | 22.85% | 2.00% | 2.00% | 93.01% | 92.89% |
| $H_2O$ | — | — | 25.11% | 24.70% | 1.00% | 1.00% | 3.92% | 3.96% |
| $O_2$ | — | — | — | — | — | — | — | — |
| $CH_4$ | — | — | 0.02% | 0.94% | — | — | — | — |
| $N_2$ | — | — | 0.82% | 1.02% | — | — | 2.55% | 2.75% |
| Ar | — | — | 0.69% | 0.83% | — | — | — | — |

TABLE 6B-continued

Composition of process streams and flow rates.

| T [° C.] | Methanol Synthesis | | WGS Outlet | | $H_2$ Production | | $CO_2$ Storage | |
|---|---|---|---|---|---|---|---|---|
| | Case 1 | Case 2 | Case 1 | Case 2 | Case 1 | Case 2 | Case 1 | Case 2 |
| $CH_3OH$ | 99.27% | 99.25% | — | — | — | — | — | — |
| Others | 0.73% | 0.75% | 0.11% | 0.11% | — | — | 0.33% | 0.14% |

Figure 8:
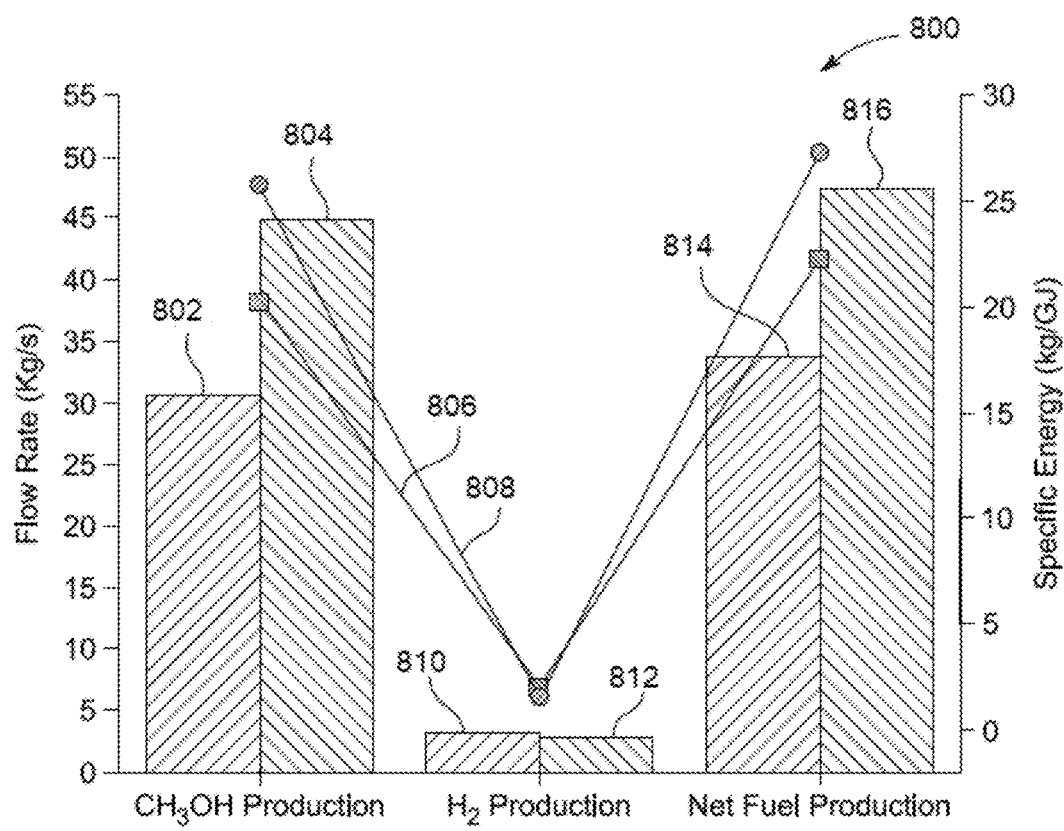
FIG. 8 is a graphical representation of the methanol and hydrogen production rates with specific energy requirements, according to certain embodiments.
Figure 9:
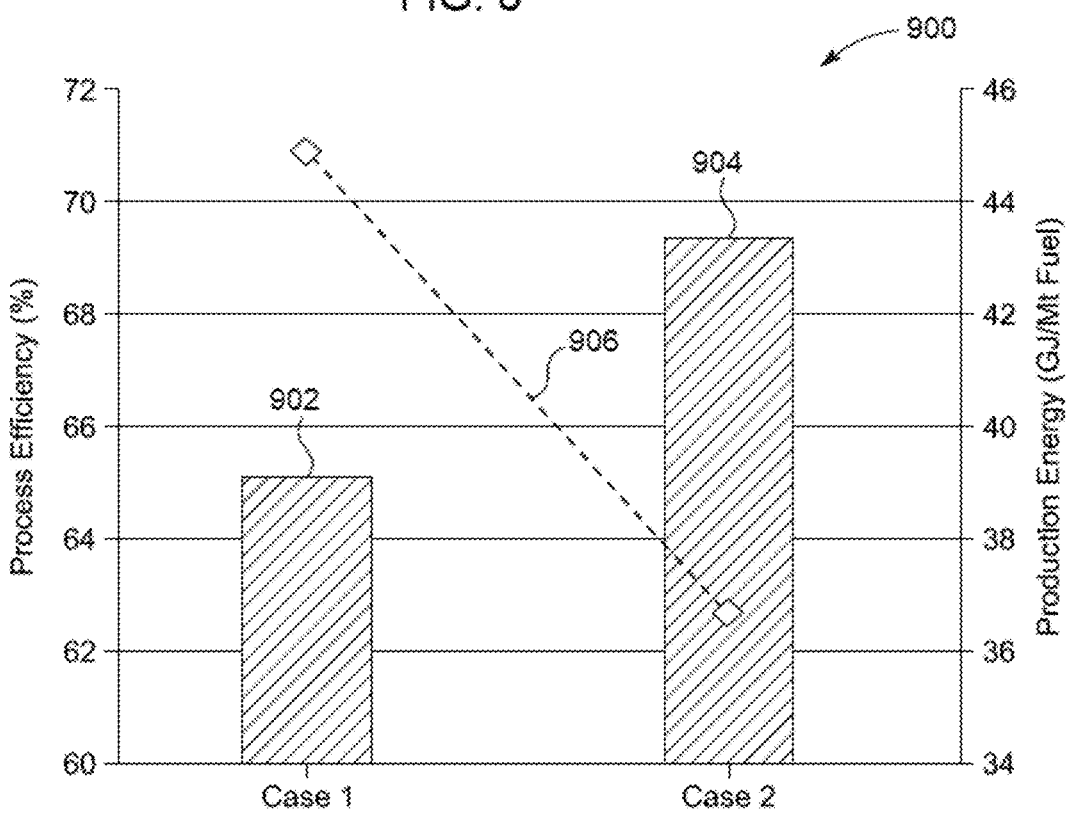
FIG. 9 is a graphical representation of process performance and energy analysis, with the case 1 system and the case 2 system, according to certain embodiments.
Figure 10:
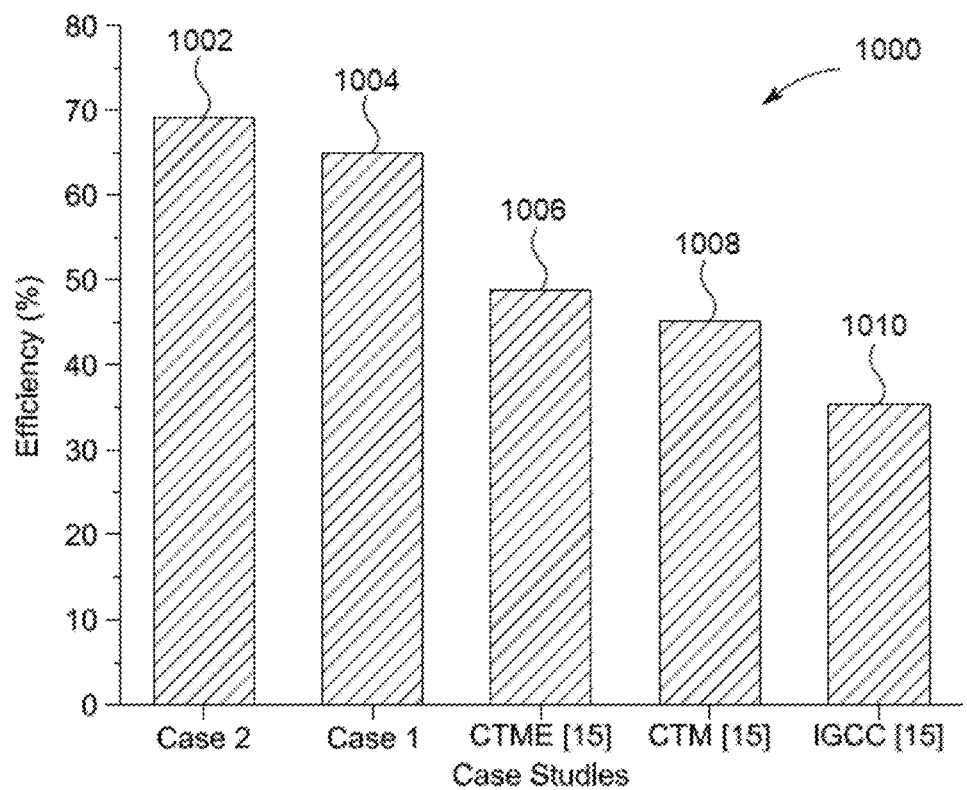
FIG. 10 illustrate a comparison of process efficiencies with literature, according to certain embodiments.

The comparative analysis showed that methanol production rates are 45.8% higher in case 2 due to higher HCR in the synthesis gas, whereas the hydrogen production in case 2 is less compared to case 1. FIG. 8 represents the results 800, considering that both methanol and $H_2$ are cleaner fuels, the specific energy requirements for dual fuel production (methanol and $H_2$) also been estimated in case 1 806 and case 2 808. The results 800 in FIG. 8 represent the flow rate of methanol 802 and 804, $H_2$ 810 and 812 and net fuel 814 and 816 production for case 1 and case 2 respectively in sync with the energy requirement 806 and 808 for case 1 and case 2 respectively. Table 7 also highlights some of the key technical performance indicators to describe the performance of case 1 and case 2. For instance, the specific energy requirement for methanol and $H_2$ production for case 1 806 was calculated as 20.21 kilograms per gigajoule (kg/GJ) and 2.07 kg/GJ, respectively. On the other hand, the specific energy requirement for the methanol and $H_2$ production for case 2 808 is 25.77 kg/GJ and 1.51 kg/GJ, respectively. The results also showed that the specific production energy requirement for fuel (methanol and $H_2$) in case 1 and case 2 is 22.28 kg/GJ and 27.27 kg/GJ, respectively, which shows that case 2 reserves the potential to generate 22.4% more fuel for each unit of energy (GJ) consumed. Similarly, the efficiency of case 1 and case 2 has been evaluated based on the thermal energy of coal and natural gas, which was used as a feedstock, and the thermal energy of the methanol and $H_2$ produced. It may be observed from the results that the overall process efficiency of case 1 and case 2 is 65.1% and 69.4%, respectively. FIG. 9, 900 represents process performance and energy analysis. The specific production energy 906 requirement for case 1 902 and case 2 904 were calculated as 44.88 GJ/MT and 36.67 GJ/MT, respectively, which shows a decline in the energy consumption up to 18.3% for the case 2 902. FIG. 10, 1000 represents the comparison of case 1 1004 and case 2 1002 with the coal to methanol (CTM), coal to methanol and electricity 1006 (CTME), and integrated gasification and combined cycle unit 1010 (IGCC) processes in terms of process efficiencies. Comparative analysis showed that the developed processes exhibit better process efficiencies than the standalone CTM 1008, CTME 1006, and IGCC 1010 processes.

TABLE 7

Thermal energy and process efficiency
Thermal energy and process efficiency

| Parameters | Units | Case 1 | Case 2 |
|---|---|---|---|
| Net energy consumed | MWth | 1519.19 | 1737.56 |
| Thermal energy of $H_2$ produced | MWth | 377.48 | 314.13 |
| Thermal energy of $CH_3OH$ produced | MWth | 611.09 | 890.88 |
| Thermal energy of fuel produced ($H_2$ and $CH_3OH$) | MWth | 988.57 | 1205.01 |

TABLE 7-continued

Thermal energy and process efficiency
Thermal energy and process efficiency

| Parameters | Units | Case 1 | Case 2 |
|---|---|---|---|
| Specific production energy ($CH_3OH$) | kg/MJ | 0.0202 | 0.0258 |
| Specific production energy ($H_2$) | kg/MJ | 0.0021 | 0.0015 |
| Specific production energy ($H_2$ and $CH_3OH$) | kg/MJ | 0.0223 | 0.0273 |
| Net process efficiency | η | 65.07% | 69.35% |

Carbon Conversion and $CO_2$ Specific Emissions

Figure 11:
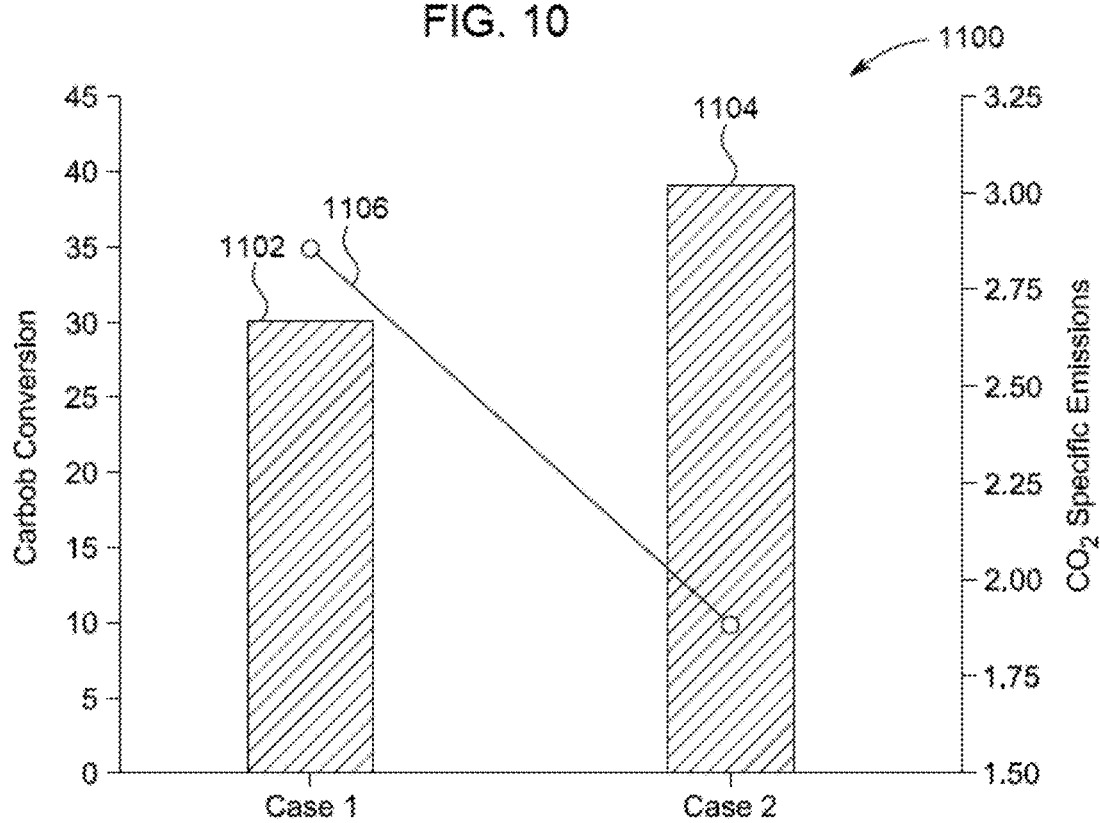
FIG. 11 illustrate carbon conversions and $CO_2$ specific emissions analysis, according to certain embodiments.

Considering the process sustainability and clean operation, carbon conversion and $CO_2$ specific emissions are usually considered as the important process indicators to analyze the process performance. Carbon conversion efficiency may be calculated based on carbon contained in the feedstock in any form ($CH_4$, CO, $CO_2$, etc.) and the conversion of carbon into the product, which was mainly methanol in the present disclosure. FIG. 11, results 1100 represents the carbon conversion efficiency for case 1 1102 and case 2 1104, respectively. From the graph 1100 it can be observed that the carbon conversion efficiency for case 1 1102 was found to be 29.6% and 39.4% for case 2 1104, respectively. Case 2 1104 showed almost 10% higher carbon conversion efficiency. Similarly, $CO_2$-specific emissions 1106 are also an important indicator to estimate the $CO_2$ generated for each unit of fuel produced, as shown in Equation. (7). The $CO_2$ capture rate in both cases is specified as 90%, where methanol is used as a solvent for $CO_2$ capture. The results in FIG. 11 showed that $CO_2$-specific emissions 1106 in terms of uncaptured $CO_2$ for each unit of fuel ($H_2$ and methanol) produced are estimated as 0.31 and 0.19 for case 1 1102 and case 2 1104, respectively. The comparative analysis showed that case 2 1104 offers higher carbon conversion efficiencies and reduces the $CO_2$-specific emissions 1106 by 38.7% for each unit of fuel (methanol and $H_2$) produced.

Effect of Natural Gas Flow Rate on Methanol and $H_2$ Production

Figure 12:
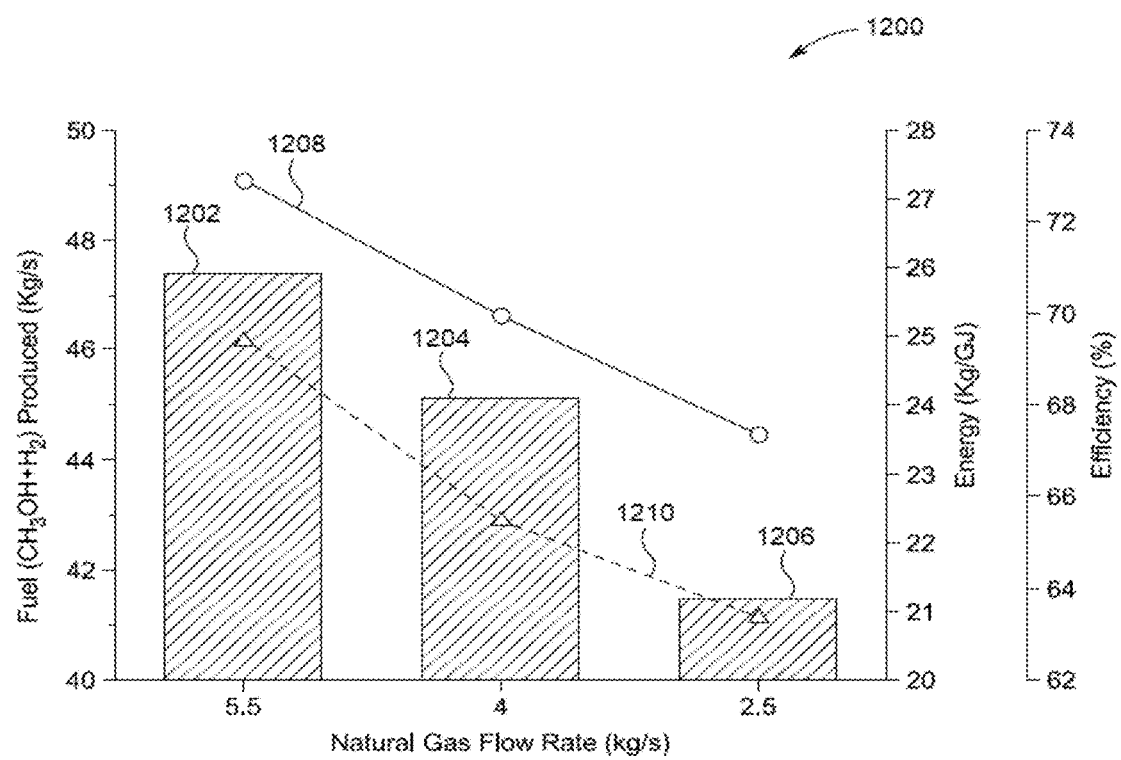
FIG. 12 illustrates the impact of natural gas flow rate on the performance of case 2, according to certain embodiments.

The natural gas has been used in case 2 for steam-methane reforming to generate additional synthesis gas and may be considered one of the most critical factors affecting the overall process performance of case 2. The sensitivity analysis has been performed on the flow rate of natural gas in case 2 to analyze its impact on the methanol and hydrogen production rates, the specific energy requirement for fuel production, and its effect on the overall process performance. FIG. 12 represents the effect of natural gas flow rate on the methanol and $H_2$ production rates and other process performance indicators. The results 1200 showed that the energy 1208 (methanol and $H_2$) production rates dropped sharply with fuel 1202, 1204 and 1206 (natural gas) flow rates. The drop in the fuel 1202, 1204 and 1206 (natural gas) flow rate results in the reduction of synthesis gas formation followed by the decline in HCR in the synthesis gas at the inlet of the methanol reactor. The decline in HCR in the synthesis gas also consumes more energy 1208, which ultimately reduces the methanol, and $H_2$ production per GJ of energy 1208 consumed. The results in FIG. 12 also showed that the efficiency 1210 of case 2 is highly affected by the natural gas flow rate, where the reduction of natural gas flow rate from 5.5 kg/s to 2.5 kg/s reduces the overall process efficiency 1210 by 6.0%.

Impact of $H_2$ Recycling on Methanol and $H_2$ Production

Figure 13:
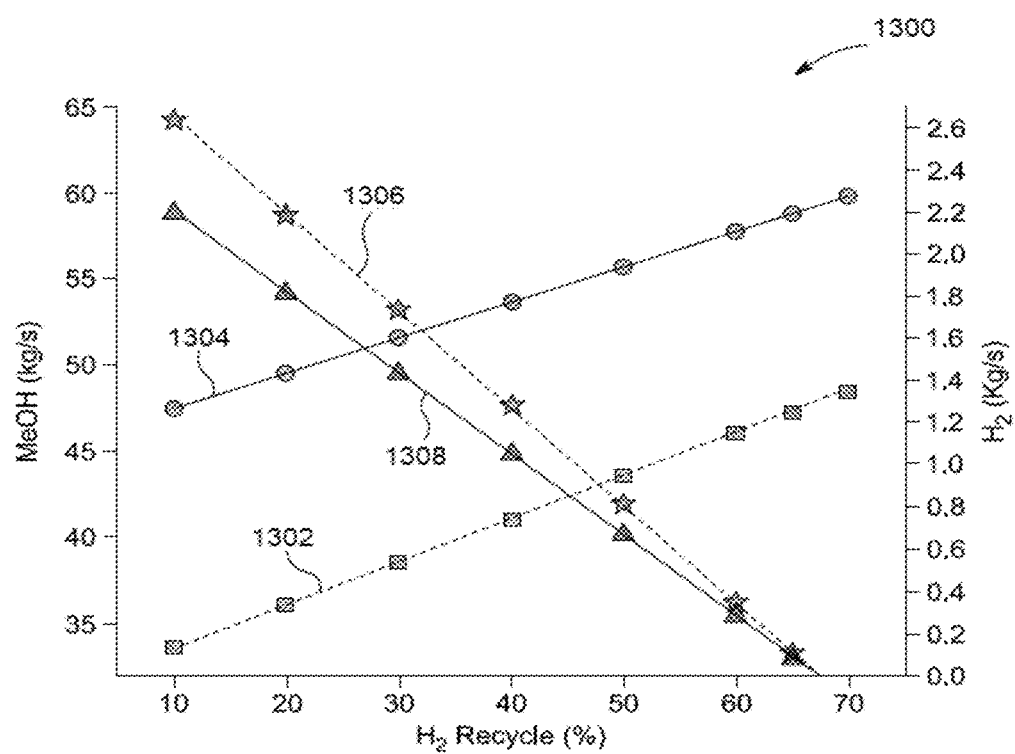
FIG. 13 illustrates the effect of $H_2$ recycle rate on the methanol and hydrogen production, according to certain embodiments.

The methanol and $H_2$ production from the case 1 and case 2 process systems highly depends on the synthesis gas production, especially the HCR in the synthesis gas. The sensitivity analysis has been performed on the $H_2$ recycle from 10 to 70% in the methanol synthesis model to see its effect on the net methanol and $H_2$ production rates. The results 1300 are represented in FIG. 13. The results showed that the methanol production rates might be significantly increased with an increase in $H_2$ recycling in case 1 1306 and case 2 1308. As more of the $H_2$ in the synthesis gas was consumed in the methanol synthesis, the uncovered amount of $H_2$ was reduced in case 1 1306 and case 2 1308. The results showed that the methanol production has been increased from 30.71 kg/s to 47.6 kg/s for case 1 1302 and from 44.77 kg/s to 58.9 kg/s for case 2 1304. However, the $H_2$ production has shown a reduction from 3.15 Kg/s and 2.62 kg/s to nearly zero-kg/s for both case 1 1306 and case 2, 1308 respectively, as all the $H_2$ is consumed in the methanol synthesis. The comparative analysis showed that increasing the $H_2$ recycling from 10 to 70% in case 1 1306 and case 2 1308 increases the methanol synthesis up to 54.9% and 31.6% for case 1 1302 and case 2 1304, respectively. It may be seen from the results that the maximum $H_2$ recycling may be increased up to 70% for the maximum utilization of $H_2$ in methanol production.

Impact of Using High Purity (99%) Oxygen on the Process Performance

The air separation unit (ASU) is one of the energy-intensive unit in the coal-gasification processes. Therefore, the sensitivity analysis was performed to see the impact of manipulating the oxygen purity levels from 95% to 99% on the synthesis gas composition and fuel ($H_2$ and methanol) production energy. Table 8 represents the effect of using 95% and 99% pure oxygen for the gasification process and its impact on the fuel production energy. The results showed that increasing the oxygen purity from 95% to 99% slightly increases the CO and $H_2$ content in the synthesis gas, which increases the synthesis gas cold-gas efficiency (CGE) up to 1.7%. However, the fuel production rates for each unit of energy consumed using 99% pure $O_2$ for case 1 and case 2 is estimated as 0.0285 kg/MJ and 0.0344 kg/MJ, respectively. While comparing the results on using 95% and 99% pure $O_2$ in the process models, it is revealed that the production energy of the fuels ($H_2$ and methanol) is increased up to 28% and 26% in case 1 and case 2, respectively. This increase in fuel production energy is the higher energy consumption in the production of 99% pure $O_2$.

TABLE 8

Impact of oxygen purity on the synthesis gas composition and fuel production energy.

| | Case 1 / Case 2 | | |
|---|---|---|---|
| Oxygen Purity (%) | 95 | 99 | |
| Syngas Composition (Gasifier Outlet) | Mole % | | Relative Difference |
| CO | 39.31% | 39.65% | 0.34% |
| $CO_2$ | 10.02% | 10.06% | 0.04% |
| $H_2$ | 30.12% | 30.41% | 0.28% |
| $H_2O$ | 18.07% | 18.15% | 0.09% |
| $CH_4$ | 0.02% | 0.02% | 0.00% |
| $H_2S$ | 0.71% | 0.72% | 0.01% |
| $N_2$ | 0.87% | 0.86% | −0.01% |
| Others | 0.87% | 0.13% | −0.74% |
| Heating Value (MJ/kg) | 10.02 | 10.19 | 17.20% |
| Fuel ($H_2$ and $CH_3OH$) production Energy (kg/MJ) | | | |
| Case 1 | 0.0223 | 0.0285 | 28.00% |
| Case 2 | 0.0273 | 0.0344 | 26.00% |

Capital and Operational Cost Estimation

A capital expenditure (CAPEX) and an operational expenditure (OPEX) highly reflects the cost of the final product. The CAPEX mainly involves the equipment, installation, piping, civil structure, and erection cost, whereas the OPEX consists of the cost of feedstocks, catalyst, utilities, etc. To maintain the consistency of the economic analysis, utility/offsite, contingency, permitting, and maintenance costs are taken as 25%, 15%, 5%, and 2%, respectively, of the total installed cost. All the equipment has been sized using the Aspen Plus sizing tool by specifying the flow rate of each stream. The CAPEX of the equipment has been estimated by Eq. (9), where x represents the capacity factor, and CEPCI represents the Chemical Engineering Plant Cost Index. The value of the capacity factor has been taken as 0.9 to handle the maximum cost variations, and the CEPCI new is taken as 618. Some of the economic assumptions are provided in Table 9, which has been used to estimate the OPEX for both cases.

$$Cost_{New} = Cost_{Old} \times \left(\frac{Capacity_{New}}{Capacity_{Old}}\right)^x \times \frac{CEPCI_{New}}{CEPCI_{Old}} \quad (9)$$

TABLE 9

Economic assumptions
Economic assumptions

| | |
|---|---|
| Coal Price | 2.2 €/GJ |
| Natural Gas | 5 €/GJ |
| Boiler Feed Water (5% recharge) | 0.33 €/m3 |
| Cooling Water price | 0.01 €/t |
| Annual Operating Hours | 7000 |
| Plant Life | 30 Years |
| Plant construction time | 3 Years |
| Administration | 30% Labor Cost |
| Labor Cost | 45,000 €/Person |
| Discount rate | 8% |
| Waste Disposal | 10 €/t |
| Maintenance | 3.5% of OPEX |
| Coal Price | 2.2 €/GJ |
| Natural Gas | 5 €/GJ |
| Boiler Feed Water (5% recharge) | 0.33 €/m3 |
| Cooling Water price | 0.01 €/t |
| Annual Operating Hours | 7000 |
| Plant Life | 30 Years |

TABLE 9-continued

Economic assumptions
Economic assumptions

| | |
|---|---|
| Plant construction time | 3 Years |
| Administration | 30% Labor Cost |
| Labor Cost | 45,000 €/Person |
| Discount rate | 8% |
| Waste Disposal | 10 €/t |
| Maintenance | 3.5% of OPEX |

Table 10 highlights both the CAPEX and OPEX for case 1 and case 2. The results showed that the CAPEX for the case 1 and case 2 is 1664 M€ and 2058 M€. The higher CAPEX of case 2 is due to installing additional natural gas reforming unit and the associated heat exchanger network. Moreover, the flow rate of the synthesis gas in case 2 is much higher than case 1, which ultimately increased the synthesis gas flow rates in the equipment and, in turn increased the overall process's CAPEX. Similarly, the OPEX per year required for case 1 and 2 has been estimated as 187 M€ and 226 M€, respectively. It may be concluded that the installation of the reforming unit in case 2 requires an additional natural gas that not only increased the boiler feed water (BFW) requirements but also increased the catalyst requirements for the natural gas reforming and methanol production units.

TABLE 10

Estimation and comparison of capital cost expenditures.
Estimation and comparison of capital cost expenditures.

| CAPEX Calculation | Case 1 (M€) | Case 2 (M€) |
|---|---|---|
| Equipment and Installation Cost | 1540.79 | 1905.17 |
| Contingency Cost (15%) | 231.12 | 285.78 |
| Permitting (5%) | 77.04 | 95.26 |
| Salvage (10%) | 184.89 | 228.62 |
| Total CAPEX | 1664.05 | 2057.59 |

| OPEX Calculation | Case 1 (M€/Year) | Case 2 (M€/Year) |
|---|---|---|
| Maintenance Cost (2% of Equipment and Installed Cost) | 30.82 | 38.1 |
| Labor Cost | 4.5 | 4.5 |
| Administrative, support & overhead cost | 1.35 | 1.35 |
| Fixed OPEX | 36.67 | 43.95 |
| Natural Gas | — | 32.89 |
| Coal | 101.87 | 101.87 |
| Boiler Feed Water (BFW) | 5.91 | 5.93 |
| Reforming Catalyst | — | 0.02 |
| Methanol Catalyst | 0.17 | 1.11 |
| $O_2$ for Gasification | 26.38 | 26.38 |
| Waste Disposal | 15.67 | 15.67 |
| Energy Saving | — | 1.52 |
| Variable OPEX | 150 | 182.36 |
| Total OPEX (Fixed þ Variable)/Year | 186.67 | 226.31 |

Some of the economic indicators including the CAPEX and OPEX for each metric ton (MT) of fuel (methanol and $H_2$) production has been also estimated as shown in Table 11. The results showed that the CAPEX per MT for the case 1 and case 2 is 65.0 M€ and 57.44 M€, respectively. Similarly, the OPEX per MT for the case 1 and case 2 is estimated as 218.81 M€ and 189.52 M€, respectively. It has been further analyzed from the results that although the CAPEX and OPEX requirements for the case 2 is higher than the case 1 but the CAPEX and OPEX per MT of the fuel production is significantly reduced for the case 2 as compared to case 1 due to higher production rates and process efficiencies.

TABLE 11

Evaluation of economic indicators and breakdown of MSP of the fuels.
Evaluation of economic indicators and breakdown of MSP of the fuels.

| | Units | Case 1 | Case2 |
|---|---|---|---|
| CAPEX/MT | Euro/MT | 65.02 | 57.44 |
| OPEX/MT | Euro/MT | 218.81 | 189.52 |
| Total (CAPEX + OPEX) | Euro/MT | 283.83 | 246.96 |
| Interest rate addition (10%) | Euro/MT | 28.38 | 24.70 |
| Selling Fuel Price ($H_2$ + $CH_3OH$) | Euro/MT | 312.21 | 271.65 |
| Selling Price of Methanol | Euro/MT | 281.73 | 225.19 |
| Selling Price of $H_2$ | Euro/MT | 30.48 | 46.46 |

Production Cost of Fuel (Methanol and $H_2$) and Project Feasibility

A total production cost (TPC) and minimum selling price (MSP) are few of the most important parameter to analyze the competitiveness of the process with the other conventional processes. The simulation results are used to estimate the consumption of the feedstocks, utilities, catalyst followed by the production rates of the methanol and $H_2$. Using all the information of the CAPEX and OPEX requirements, the TPC calculated for each MT of fuel produced for case 1 and case 2 is 283.83 € and 246.96 €, respectively. The results also showed that TPC for case 2 is almost 13% less than the case 1. The interest rate on the TPC is taken as 10% to estimate the MSP of the fuel. Table 11 also represents the breakdown of MSP of the fuels for both cases. Overall, it may be seen from results that the MSP of combined fuels (methanol and $H_2$) is lower in case 2 compared to case 1, which in turn reflects the cost competitiveness of the process. Furthermore, it may be seen from results that there is a tradeoff between the methanol and $H_2$ selling prices. Case 2 represents the lower MSP of the methanol compared to the case 1, whereas case 1 showed the lower MSP of the $H_2$ compared to the case 2. Keeping in view the overall process efficiencies and TPC of both fuels, case 2 has shown the better process performance with the reduction in TPC and MSP. The $H_2$ recirculation rates may be also manipulated to control the methanol and $H_2$ production rates according to the market needs in both the cases.

Figure 14A:
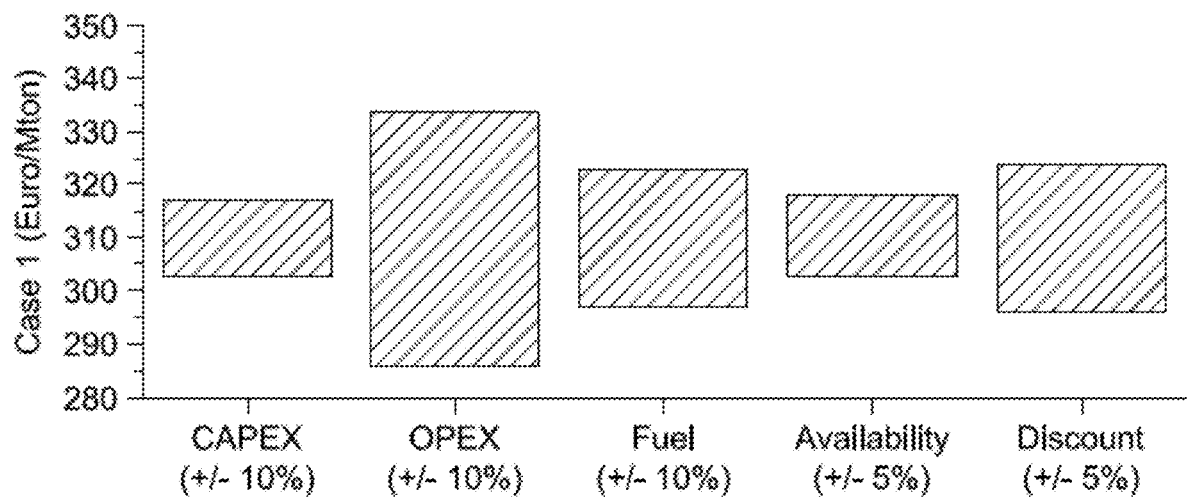
FIG. 14A illustrates sensitivity analysis for estimating a minimum support price (MSP) of fuels for Case 1, according to certain embodiments.
Figure 14B:
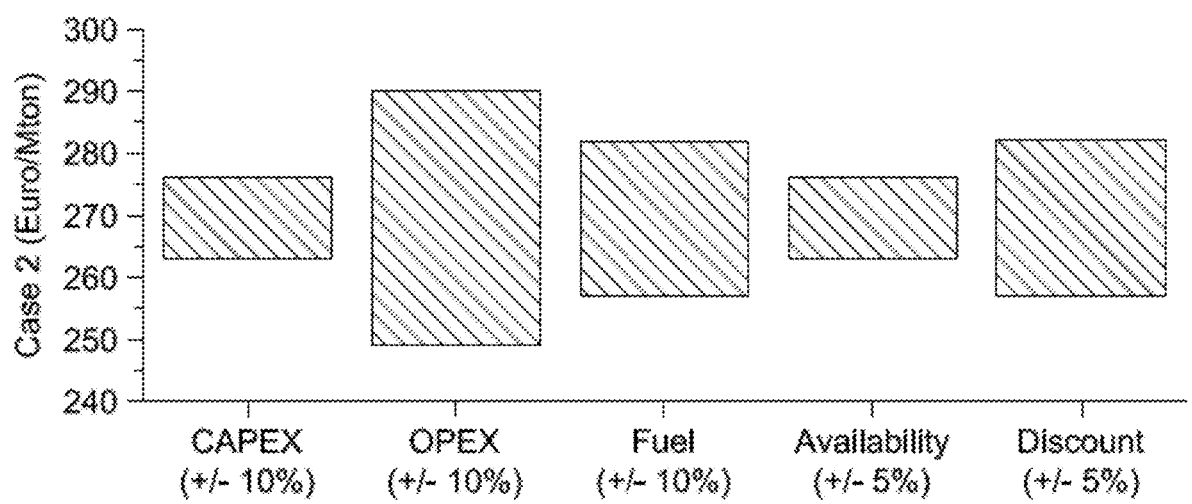
FIG. 14B illustrates sensitivity analysis for estimating MSP of fuels for Case 2, according to certain embodiments.

The cash flow analysis of both cases, case 1 and case 2 was calculated, and it was observed that the payback time of the project for both the cases is around nine years, whereas the case 2 reserves the higher rate on return on investments compared to case 1 during the lifetime of the project. The sensitivity analysis has also been performed to analyze the impact of cost variations (0-10%) due to equipment cost, feedstock and fuel cost, plant operational time, and the interest rates on the MSP of the fuel. FIGS. 14A-14B represent the cost variation parameters and their impact on the MSP of the fuel (methanol and $H_2$) in case 1 and case 2 respectively. The results showed that the OPEX variation highly affects the MSP of the fuels, whereas the CAPEX variations have the most negligible effect on the MSP of fuels. On the other hand, slight variations in the interest rate may highly affect the fuel's MSP in both cases.

In the present disclosure, two process models are developed and techno-economically compared for dual production of methanol and $H_2$. Case 1 represents the coal to methanol and $H_2$ production model, whereas case 2 represents the coal gasification and the natural gas reforming integrated based models. The two cases are compared in terms of methanol and $H_2$ production rates, specific production energy requirements, carbon conversion, $CO_2$ emissions, and the production and selling costs which are provided as follows:

1. Both methanol and $H_2$ are treated as cleaner fuels. The net production rates of fuel (methanol and $H_2$) for case 1 and case 2 is calculated as 33.85 kg/s and 47.39 kg/s, respectively.

2. The fuel production for each GJ of energy consumed for case 1 and case 2 was estimated as 22.28 kg and 27.22 kg, respectively.

3. Case 2 showed 10% higher carbon conversion efficiency and lowered the $CO_2$ specific emissions by 38.7% compared to case 1. The overall efficiency for cases 1 and 2 was also calculated as 65.1% and 69.4%, respectively.

4. The process performance of case 2 was dependent on the natural gas flow, the rate in the reforming unit, where the overall process efficiency reduced up to 6% with almost 55% reduction of the natural gas flow rate.

5. The methanol production rates were affected by the $H_2$ recycle in both cases, $H_2$ recycling from 10 to 70% increased the methanol synthesis up to 54.9% and 31.6% for case 1 and case 2, respectively.

6. By incorporating the CAPEX and OPEX requirements, the total production cost of fuel (methanol and $H_2$) is estimated as 283.73 M€ and 246.96 M€ for each MT of fuel produced.

7. Case 2 showed the better process performance compared to case 1 in terms of both production energy requirements and fuel production costs, thereby the better project feasibility during the project's lifetime.

While comparing the process models in terms of process performance and economics, it has been analyzed that integrating state-of-art technologies using fuel-mix and energy switch systems may improve process sustainability. The discussed models may further improve the process performance while reducing the energy requirements and carbon footprint. In the present disclosure, coal and natural gas feedstocks are used for the MeOH synthesis and electricity production by using the parallel system integrations between the gasification and reforming technologies. This allows utilizing the heat energy from the gasification unit into the reforming unit to sustain the high enthalpy SMR reactions. This integration reduces the overall process energy requirements, while also enhancing the syngas production with the higher HCR ratio system.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method of preparing methanol, comprising:
gasifying coal to produce a coal gas comprising hydrogen and carbon monoxide;
transferring heat from the coal gas to a natural gas reforming mixture comprising water and methane, thereby cooling the coal gas and heating the natural gas reforming mixture;
reforming the natural gas reforming mixture to form a reformed natural gas comprising hydrogen and carbon monoxide;
mixing the coal gas, the reformed natural gas, a recycled gas, and optionally hydrogen to form a synthesis gas;
removing carbon dioxide from the synthesis gas;
reacting the synthesis gas to form methanol and a waste gas comprising water, carbon monoxide, and carbon dioxide;
separating the methanol and the waste gas;
removing hydrogen from the waste gas to produce a dehydrogenated waste gas; and
subjecting the dehydrogenated waste gas to a water-gas shift reaction to produce the recycled gas, wherein the recycled gas comprises 40 to 60 mol % hydrogen, 20 to 25 mol % carbon dioxide, 20 to 30 mol % water, and carbon monoxide,
wherein the hydrogen removed from the waste gas is stored and/or added to the synthesis gas in the mixing.

2. The method of claim 1, further comprising removing sulfur-containing species from the coal gas prior to mixing.

3. The method of claim 1, wherein the gasifying is performed at 1200 to 1550° C. and 45 to 67 bar.

4. The method of claim 1, wherein the reforming is performed at 900 to 1200° C. and 32 to 68 bar.

5. The method of claim 1, wherein the reacting is performed at 125 to 275° C. and 45 to 65 bar.

6. The method of claim 1, wherein the synthesis gas has a hydrogen to carbon ratio of 45:55 to 55:45 and an HHV of 16.5 to 20.5 MJ/kg.

7. The method of claim 1, having a carbon conversion efficiency of 32.5 to 47.5%.

8. The method of claim 1, having a production energy of 34 to 40 GJ/Mt total fuel, the total fuel being the sum of the methanol produced and hydrogen produced.

9. The method of claim 1, having a process efficiency of 66 to 74%, the process efficiency calculated by:

$$\text{Process Efficiency}(\eta net) = \frac{\text{Methanol thermal energy }[MWth] + \text{H2 thermal energy }[MWth]}{\text{Feed stock thermal energy }[MWth] + \text{Energy consumed }[MWth]} \times 100.$$

10. The method of claim 1, wherein the coal comprises:
44.19 wt % fixed carbon;
34.99 wt % volatile matter; and
a mixture comprising water, sulfur, and ash to balance, based on a total weight of coal.

11. The method of claim 1, wherein the coal comprises 63.75 wt % carbon, based on a total weight of coal.

12. The method of claim 1, wherein the coal has a lower heating value of 26151 kJ/kg.

13. The method of claim 1, having a thermal energy of hydrogen and methanol produced of 988.57 to 1205.01 MWth.

14. The method of claim 1, having a specific production energy of methanol of 0.0202 to 0.0258 kg/MJ and a specific production energy of hydrogen of 0.0021 to 0.0015 kg/MJ.

15. The method of claim 1, further comprising:
removing sulfur-containing species from the coal gas prior to mixing, and
removing carbon dioxide from the synthesis gas prior to reacting, wherein:
the gasifying is performed at 1200 to 1550° C. and 45 to 67 bar,
the reforming is performed at 900 to 1200° C. and 32 to 68 bar,
the reacting is performed at 125 to 275° C. and 45 to 65 bar,
the synthesis gas has a hydrogen to carbon ratio of 45:55 to 55:45 and an HHV of 16.5 to 20.5 MJ/kg, the method has a carbon conversion efficiency of 32.5 to 47.5%, the method has a production energy of 34 to 40 GJ/Mt total fuel, the total fuel being the sum of the methanol produced and hydrogen produced, and the method has a process efficiency of 66 to 74%, the process efficiency calculated by:

$$\text{Process Efficiency}(\eta net) = \frac{\text{Methanol thermal energy } [MWth] + \text{H2 thermal energy } [MWth]}{\text{Feed stock thermal energy } [MWth] + \text{Energy consumed } [MWth]} \times 100.$$

16. The method of claim 1, further comprising:

removing sulfur-containing species from the coal gas prior to mixing, and removing carbon dioxide from the synthesis gas prior to reacting, wherein:

the gasifying is performed at 1325 to 1425° C. and 53 to 59 bar, the reforming is performed at 930 to 1050° C. and 52 to 58 bar, the reacting is performed at 175 to 225° C. and 52 to 58 bar, the synthesis gas has a hydrogen to carbon ratio of 50:49 to 52.5:47.5 and an HHV of 18.25 to 19.5 MJ/kg, the method has a carbon conversion efficiency of 37.0 to 43.0%, the method has a production energy of 35.5 to 37.75 GJ/Mt total fuel, the total fuel being the sum of the methanol produced and hydrogen produced, and the method has a process efficiency of 68.5 to 70.5%, the process efficiency calculated by:

$$\text{Process Efficiency}(\eta net) = \frac{\text{Methanol thermal energy } [MWth] + \text{H2 thermal energy } [MWth]}{\text{Feed stock thermal energy } [MWth] + \text{Energy consumed } [MWth]} \times 100.$$

17. The method of claim 1, further comprising, prior to the mixing, removing water from the recycled gas.

* * * * *